(12) United States Patent
Rocco et al.

(10) Patent No.: US 12,318,389 B2
(45) Date of Patent: Jun. 3, 2025

(54) FORMULATIONS OF AN AXL/MER INHIBITOR

(71) Applicant: Incyte Corporation, Wilmington, DE (US)

(72) Inventors: William L. Rocco, Reading, PA (US); Francis X. Muller, Chester Springs, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 18/428,522

(22) Filed: Jan. 31, 2024

(65) Prior Publication Data

US 2024/0423991 A1 Dec. 26, 2024

Related U.S. Application Data

(63) Continuation of application No. 17/563,282, filed on Dec. 28, 2021, now Pat. No. 11,918,585, which is a continuation of application No. 16/456,547, filed on Jun. 28, 2019, now Pat. No. 11,241,438.

(60) Provisional application No. 62/692,210, filed on Jun. 29, 2018.

(51) Int. Cl.
| | | |
|---|---|---|
| A61K 31/53 | (2006.01) | |
| A61K 9/20 | (2006.01) | |
| A61K 9/48 | (2006.01) | |
| A61K 47/12 | (2006.01) | |
| A61P 35/00 | (2006.01) | |

(52) U.S. Cl.
CPC ............ *A61K 31/53* (2013.01); *A61K 9/2009* (2013.01); *A61K 9/2018* (2013.01); *A61K 9/2031* (2013.01); *A61K 9/485* (2013.01); *A61K 9/4858* (2013.01); *A61K 9/4866* (2013.01); *A61K 47/12* (2013.01); *C07B 2200/13* (2013.01)

(58) Field of Classification Search
CPC .............................. A61K 31/53; A61P 35/00
USPC ......................................................... 514/243
See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 5,057,313 A | 10/1991 | Shih et al. |
| 5,156,840 A | 10/1992 | Goers et al. |
| 5,179,017 A | 1/1993 | Axel et al. |
| 5,530,101 A | 6/1996 | Queen et al. |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,714,350 A | 2/1998 | Co et al. |
| 5,731,168 A | 3/1998 | Carter et al. |
| 5,849,992 A | 12/1998 | Meade et al. |
| 5,859,205 A | 1/1999 | Adair et al. |
| 5,869,046 A | 2/1999 | Presta et al. |
| 6,300,064 B1 | 10/2001 | Knappik et al. |
| 6,350,861 B1 | 2/2002 | Co et al. |
| 6,407,213 B1 | 6/2002 | Carter et al. |
| 8,791,257 B2 | 7/2014 | Markwalder et al. |
| 9,708,333 B2 | 7/2017 | Li et al. |
| 9,840,503 B2 | 12/2017 | Sun et al. |
| 9,981,975 B2 | 5/2018 | Li et al. |
| 10,005,788 B2 | 6/2018 | Li et al. |
| 10,053,465 B2 | 8/2018 | Li et al. |
| 10,138,248 B2 | 11/2018 | Buesking et al. |
| 10,442,810 B2 | 10/2019 | Li et al. |
| 10,519,163 B2 | 12/2019 | Li et al. |
| 10,633,387 B2 | 4/2020 | Jia et al. |
| 10,844,069 B2 | 11/2020 | Li et al. |
| 11,104,682 B2 | 8/2021 | Jia et al. |
| 11,136,326 B2 | 10/2021 | Li et al. |
| 11,241,438 B2 | 2/2022 | Rocco et al. |
| 11,591,338 B2 | 2/2023 | Li et al. |
| 11,918,585 B2 | 3/2024 | Rocco et al. |
| 2005/0008625 A1 | 1/2005 | Balint et al. |
| 2005/0037000 A1 | 2/2005 | Stavenhagen et al. |
| 2005/0079574 A1 | 4/2005 | Bond |
| 2006/0235031 A1 | 10/2006 | Arnold et al. |
| 2008/0045528 A1 | 2/2008 | Sutton et al. |
| 2010/0298334 A1 | 11/2010 | Rodgers et al. |
| 2011/0015212 A1 | 1/2011 | Li et al. |
| 2011/0059951 A1 | 3/2011 | Rodgers et al. |
| 2011/0183985 A1 | 7/2011 | Li et al. |
| 2011/0224190 A1 | 9/2011 | Huang et al. |
| 2012/0015937 A1 | 1/2012 | Ding et al. |

(Continued)

FOREIGN PATENT DOCUMENTS

| | | |
|---|---|---|
| CL | 2018002759 | 9/2018 |
| CL | 2018000949 | 12/2018 |

(Continued)

OTHER PUBLICATIONS

Affouard et al., "Multi-Kilo Delivery of AMG 925 Featuring a Buchwald-Hartwig Amination and Processing with Insoluble Synthetic Intermediates," Organic Process Research & Development, 2015, 19: 476-485.

(Continued)

*Primary Examiner* — Raymond J Henley, III

(74) *Attorney, Agent, or Firm* — Fish & Richardson P.C.

(57) ABSTRACT

The present application relates to pharmaceutical formulations and dosage forms of an AXL/MER inhibitor, or a pharmaceutically acceptable salt, solvate, or hydrate thereof, including methods of preparation thereof, which are useful in the treatment of AXL/MER mediated diseases such as cancer.

44 Claims, 3 Drawing Sheets

Specification includes a Sequence Listing.

(56) References Cited

U.S. PATENT DOCUMENTS

| | | |
|---|---|---|
| 2012/0088768 A1 | 4/2012 | Singh et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0184535 A1 | 7/2012 | Brzozka et al. |
| 2012/0219522 A1 | 8/2012 | Xi |
| 2012/0230993 A1 | 9/2012 | Graham et al. |
| 2012/0264740 A1 | 10/2012 | Goff et al. |
| 2012/0283261 A1 | 11/2012 | Bearss et al. |
| 2013/0018034 A1 | 1/2013 | Yao et al. |
| 2013/0018051 A1 | 1/2013 | Singh et al. |
| 2013/0045963 A1 | 2/2013 | Rodgers et al. |
| 2013/0059835 A1 | 3/2013 | Li et al. |
| 2013/0090330 A1 | 4/2013 | Ding et al. |
| 2013/0137702 A1 | 5/2013 | Steiner et al. |
| 2013/0197070 A1 | 8/2013 | De Franciscis et al. |
| 2013/0281468 A1 | 10/2013 | Goff et al. |
| 2014/0005166 A1 | 1/2014 | Rodgers et al. |
| 2014/0018365 A1 | 1/2014 | Schultz-Fademrecht et al. |
| 2014/0121198 A1 | 5/2014 | Li et al. |
| 2014/0128390 A1 | 5/2014 | Lin |
| 2014/0128400 A1 | 5/2014 | Singh et al. |
| 2014/0275023 A1 | 9/2014 | Namdev et al. |
| 2015/0031676 A1 | 1/2015 | Lobell et al. |
| 2016/0333008 A1 | 11/2016 | Sun et al. |
| 2017/0044164 A1 | 2/2017 | Li et al. |
| 2017/0057965 A1 | 3/2017 | Li et al. |
| 2017/0275290 A1 | 9/2017 | Li et al. |
| 2017/0334884 A1 | 11/2017 | Petersen |
| 2018/0009815 A1 | 1/2018 | Li et al. |
| 2018/0327412 A1 | 11/2018 | Li et al. |
| 2019/0031663 A1 | 1/2019 | Li et al. |
| 2019/0112313 A1 | 4/2019 | Jia et al. |
| 2020/0000812 A1 | 1/2020 | Rocco et al. |
| 2020/0131185 A1 | 4/2020 | Li et al. |
| 2020/0181151 A1 | 6/2020 | Li et al. |
| 2020/0347065 A1 | 11/2020 | Jia et al. |
| 2021/0147430 A1 | 5/2021 | Li et al. |
| 2021/0275666 A1 | 9/2021 | Rios-Doria |
| 2022/0227770 A1 | 7/2022 | Jia et al. |
| 2022/0273663 A1 | 9/2022 | Rocco et al. |
| 2024/0124463 A1 | 4/2024 | Li et al. |

FOREIGN PATENT DOCUMENTS

| | | |
|---|---|---|
| CL | 2019000043 | 6/2019 |
| CL | 2019000115 | 6/2019 |
| CN | 101084218 | 12/2007 |
| CN | 102408411 | 4/2012 |
| CN | 102918045 | 2/2013 |
| CN | 101641093 | 5/2013 |
| CN | 103124729 | 5/2013 |
| CN | 103608342 | 2/2014 |
| CN | 102482278 | 4/2015 |
| CN | 105732634 | 7/2016 |
| CO | 20210000923 | 4/2021 |
| EP | 0404097 | 12/1990 |
| EP | 2320902 | 5/2011 |
| EP | 2465505 | 6/2012 |
| EP | 2484679 | 8/2012 |
| EP | 2552922 | 2/2013 |
| EP | 2791140 | 10/2014 |
| EP | 2810937 | 12/2014 |
| ES | 2253774 | 6/2006 |
| ES | 2307003 | 11/2008 |
| IN | 201817040446 | 2/2019 |
| JP | H03-95163 | 4/1991 |
| JP | 2008-501703 | 1/2008 |
| JP | 2009-518303 | 5/2009 |
| JP | 2009-519222 | 5/2009 |
| JP | 2009-519905 | 5/2009 |
| JP | 2010-522742 | 7/2010 |
| JP | 2010-529196 | 8/2010 |
| JP | 2012-525400 | 10/2012 |
| JP | 2014-525902 | 10/2014 |
| JP | 2015-532287 | 11/2015 |
| JP | 2019-510043 | 4/2019 |
| JP | 2021-529765 | 11/2021 |
| KR | 2013-0141706 | 12/2013 |
| KR | 2015-0061651 | 6/2015 |
| WO | WO 1990/07861 | 7/1990 |
| WO | WO 1993/11161 | 6/1993 |
| WO | WO 2001/019828 | 3/2001 |
| WO | WO 2002/000196 | 1/2002 |
| WO | WO 2002/080975 | 10/2002 |
| WO | WO 2004/026840 | 4/2004 |
| WO | WO 2004/035580 | 4/2004 |
| WO | WO 2005/003175 | 1/2005 |
| WO | WO 2005/018572 | 3/2005 |
| WO | WO 2005/025515 | 3/2005 |
| WO | WO 2006/046023 | 5/2006 |
| WO | WO 2006/056399 | 6/2006 |
| WO | WO 2007/061737 | 5/2007 |
| WO | WO 2007/064883 | 6/2007 |
| WO | WO 2007/070514 | 6/2007 |
| WO | WO 2007/120752 | 10/2007 |
| WO | WO 2007/125315 | 11/2007 |
| WO | WO 2008/048375 | 4/2008 |
| WO | WO 2008/076392 | 6/2008 |
| WO | WO 2018/198077 | 11/2008 |
| WO | WO 2009/022354 | 2/2009 |
| WO | WO 2009/023269 | 2/2009 |
| WO | WO 2009/047514 | 4/2009 |
| WO | WO 2009/053737 | 4/2009 |
| WO | WO 2009/054864 | 4/2009 |
| WO | WO 2009/085185 | 7/2009 |
| WO | WO 2009/087225 | 7/2009 |
| WO | WO 2009/127417 | 10/2009 |
| WO | WO 2009/134723 | 11/2009 |
| WO | WO 2010/005876 | 1/2010 |
| WO | WO 2010/005879 | 1/2010 |
| WO | WO 2010/008454 | 1/2010 |
| WO | WO 2010/014755 | 2/2010 |
| WO | WO 2010/025073 | 3/2010 |
| WO | WO 2010/071885 | 6/2010 |
| WO | WO 2010/090764 | 8/2010 |
| WO | WO 2011/038185 | 3/2011 |
| WO | WO 2011/045084 | 4/2011 |
| WO | WO 2011/139273 | 11/2011 |
| WO | WO 2011/146313 | 11/2011 |
| WO | WO 2012/028332 | 3/2012 |
| WO | WO 2012/048129 | 4/2012 |
| WO | WO 2012/129344 | 9/2012 |
| WO | WO 2012/135800 | 10/2012 |
| WO | WO 2012/174082 | 12/2012 |
| WO | WO 2013/040286 | 3/2013 |
| WO | WO 2013/052417 | 4/2013 |
| WO | WO 2013/074633 | 5/2013 |
| WO | WO 2013/085802 | 6/2013 |
| WO | WO 2013/115280 | 8/2013 |
| WO | WO 2013/162061 | 10/2013 |
| WO | WO 2014/062774 | 4/2014 |
| WO | WO 2014/079545 | 5/2014 |
| WO | WO 2014/109858 | 7/2014 |
| WO | WO 2014/164729 | 10/2014 |
| WO | WO 2015/012298 | 1/2015 |
| WO | WO 2015/068767 | 5/2015 |
| WO | WO 2015/081783 | 6/2015 |
| WO | WO 2015/132799 | 9/2015 |
| WO | WO 2016/097918 | 6/2016 |
| WO | WO 2016/183071 | 11/2016 |
| WO | WO 2017/019846 | 2/2017 |
| WO | WO 2017/027717 | 2/2017 |
| WO | WO 2017/062797 | 4/2017 |
| WO | WO 2017/083788 | 5/2017 |
| WO | WO 2017/083789 | 5/2017 |
| WO | WO 2017/172596 | 10/2017 |

(56) References Cited

FOREIGN PATENT DOCUMENTS

| WO | WO 2017/184934 | 10/2017 |
|---|---|---|
| WO | WO 2019/067594 | 4/2019 |

OTHER PUBLICATIONS

Angal et al., "A single amino acid substitution abolishes the heterogeneity of chimeric mouse/human (IgG4) antibody," Mol. Immunol., 1993, 30:105-108.
Angelillo-Scherrer et al., "Role of Gas6 in erythropoiesis and anemia in mice," J. Clin. Invest., 2008, 118: 583-596.
Anonymous: "Study Record Versions History of Changes for Study: NCT03522142 A Study Exploring the Safety and Tolerability of INCB081776 in Participants With Advanced Malignancies," Mar. 20, 2020[retrieved on Jun. 4, 2021], retrieved from URL<https://clinicaltrials.gov/ct2/history/NCT03522142?A=8&8=8&C=merged#StudyPageTop>, 10 pages.
Ash and Ash, "Handbook of Pharmaceutical Additives," Gower Publishing Company, 2007, 3rd Edition, 1 page, Title Page.
Australian Office Action in Australian Application No. 2017241524, Jun. 26, 2020, 4 pages.
Australian Office Action in Australian Application No. 2019293618, dated Apr. 12, 2024, 4 pages.
Avilla et al., "Activation of TYRO3/AXL tyrosine kinase receptors in thyroid cancer," Cancer Res., Mar. 1, 2011, 71(5):1792-1804.
Badaway et al., "Salt Selection for Pharmaceutical Compounds," Preformulation in Solid Dosage Form Development(Informa Healthcare), 2008, Chapter 2.3, 63-80.
Baladi et al., "State-of-the-art of small molecule inhibitors of the TAM family: The point of view of the chemist," European Journal of Medicinal Chemistry, Oct. 2015, 105: 220-237.
Balupuri et al., "Molecular modeling study on Mer kinase inhibitors using 3D-QSAR and docking approaches," Medicinal Chemistry Research, Jul. 2015, 24(10): 3730-3742.
Bastin et al., "Salt Selection and Optimization Procedures for Pharmaceutical New Chemicalls Entities," Organic Process Research & Development, 2000, 4(5):427-435.
Ben-Batalla et al., "Axl Blockade by BGB324 Inhibits BCR-ABL Tyrosine Kinase Inhibitor-Sensitive and -Resistant Chronic Myeloid Leukemia," Clinical Cancer Research, May 1, 2017, 23(9):2289-2300.
Ben-Batalla., "Axl, a prognostic and therapeutic target in acute myeloid leukemia mediates paracrine crosstalk of leukemia cells with bone marrow stroma," Blood, Oct. 3, 2013, 122(14):2443-2452.
Berge, "Pharmaceutical Salts," Journal of Pharmaceutical Science, 1997, 66(1):1-19.
Berraondo et al., "Cytokines in clinical cancer immunotherapy," British Journal of Cancer, 2019, 120:6-15.
Better et al., "*Escherichia coli* secretion of an active chimeric antibody fragment," Science, 1988, 240:1041-1043.
Better, "Expression of engineered antibodies and antibody fragments in microorganisms," Methods in Enzymology, 1989, 178:476-496.
Bird et al., "Single chain antibody variable regions," Trends Biotechnol., Apr. 1991, 9:132-137.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chromatography—Mass Spectrometry," J. Comb. Chem., 2002, 4: 295-301.
Borovik et al., "Pyrimidines. XLIX. Synthesis of 9-phenylpyrimido[4,5-b] indoles," Izvestiya Sibirskogo Otdeleniya Akademii Nauk SSSR, Seriya Khimicheskikh Nauk , 1975, 137-41 (English abstract only).

Borovik et al., "Synthesis of 2-substituted pyrimido[4,5-b]indoles and N-phenyl-2,2-diethoxy-3-arylideneindolines," v sb., Khimiya i Farmakol. Indol'n. Soedinenii, 1975, 50 (English abstract only).
Boyd, "Some practical considerations and applications of the national cancer institute in vitro anticancer drug discovery screen," Drug Development Research, Feb. 1995, 34(2):91-109.
Brazilian Office Action in Brazilian Application No. 112018069612-9, dated Sep. 5, 2023, 8 pages (with Machine Translation).
Brazilian Office Action in Brazilian Application No. BR112020006145-0, dated Sep. 9, 2022, 5 pages (with English Translation).
Brunton et al., "Chemotherapy of Neoplastic Diseases," Goodman & Gilman's: The Pharmacological Basis of Therapeutics, 2008, pp. 853-908.
Burbridge et al., "S49076 Is a Novel Kinase Inhibitor of MET, AXL, and FGFR with Strong Preclinical Activity Alone and in Association with Bevacizumab," AACR Journals, 2013, 1749-1762.
Cancer Drug Design and Discovery, 1st ed., Neidle (ed)., 2008, p. 427.
Carter et al., "High level *Escherichia coli* expression and production of a bivalent humanized antibody fragment," Bio/Technology, 1992, 10:163-167.
Carter et al., "Humanization of an anti-p185HER2 antibody for human cancer therapy," PNAS, 1992, 89: 4285-4289.
Cecil Textbook of Medicine, edited by Bennet, J.C., and Plum F., 20th edition, vol. 1, 1004-1010, 1996.
Chambers et al., "Lymphoproliferation in CTLA-4-deficient mice is mediated by costimulation-dependent activation of CD4+ T cells," Immunity, Dec. 1997, 7(6): 885-95.
Chilean Office Action in Chilean Application No. 202003397, dated Jun. 13, 2022, 14 pages.
Chilean Office Action in Chilean Application No. 202000791, dated Jul. 15, 2021, 34 pages.
Chilean Office Action in Chilean Application No. 202201014, dated Jun. 11, 2024, 33 pages (with Machine Translation).
Chilean Office Action in Chilean Application No. 202201014, dated Sep. 5, 2023, 36 pages (with Machine Translation).
Chilean Office Action in Chilean Application No. 202202410, dated Jan. 5, 2024, 31 pages (with Machine Translation).
Chinese Office Action in Chinese Application No. 201780031476.3, dated Oct. 28, 2020, 16 pages.
Chinese Office Action in Chinese Application No. 201980055116.6, dated Jun. 22, 2022, 12 pages.
Chothia et al., "Structural repertoire of the human VH segments," J Mol Bio., 1992, 227:799-817.
Chow et al., "Engineered of Pharmaceutical Materials: an Industrial Perspective," J Pharmaceutical Sciences., Aug. 2008, 97(8):2855-2877.
Chung et al., "Synthesis of certain [6:5:6] linear tricyclic nucleosides as potential antitumor agents," Journal of Medicinal Chemistry, Nov. 1980, 23(11): 1158-66.
Co et al., "A humanized antibody specific for the platelet integrin gpIIb/IIIa," J Immunol., Mar. 15, 1994, 152(6):2968-2976 (Abstract Only).
Cohen., "The development and therapeutic potential of protein kinase inhibitors," Current Opinion in Chemical Biology, 1999, 3: 459-465, 1999.
Colombian Office Action in Colombian Application No. 2021/0000923, dated Apr. 26, 2023, 22 pages (with English translation).
Colombian Office Action in Colombian Application No. NC2018/0011550, dated May 29, 2020, 16 pages.
Colombian Office Action in Colombian Application No. NC2020/0005009, dated May 27, 2022, 22 pages.
Colombian Office Action in Colombian Application No. NC2021/0004423, Aug. 2, 2021, 20 pages.
Columbian Office Action in Columbian Application No. 2020/0005009, dated Oct. 25, 2023, 27 pages (with English Translation).
Columbian Office Action in Columbian Application No. 2021/0000923, dated Sep. 24, 2023, 25 pages (with English Translation).
Cook et al., "MerTK inhibition in tumor leukocytes decreases tumor growth and metastasis," J. Clin. Invest., Aug. 2013, 123(8): 3231-42.
Cook et al., "The human immunoglobulin VH repertoire," Immunol Today., 1995, 16: 237-242.

(56) References Cited

OTHER PUBLICATIONS

Cosemans et al., "Potentiating role of Gas6 and Tryo3, Axl and Mer (TAM) receptors in human and murine platelet activation and thrombus stabilization," J. of Thrombosis and Haemostasis, 2010, 8: 1797-1808.
Costa Rican Office Action in Costa Rican Application No. 2018-0516, dated May 4, 2022, 12 pages.
Costa Rican Office Action in Costa Rican Application No. 2020-179, dated Nov. 8, 2023, 15 pages (with English Translation).
Cruz-Cabeza et al., "Facts and Fictions about Polymorphism," Chemical Society Reviews, 2015, 44:8619-8635.
Datta et al., "Crystal Structures of Drugs: Advances in Determination, Prediction and engineering," Nature, Jan. 2004, 3:42-57.
Davies et al., "Single antibody domains as small recognition units: design and in vitro antigen selection of camelized, human VH domains with improved protein stability," Protein Eng., 1996, 9(6):531-537.
Demarest et al., "Evaluation of Tyro3 expression, Gas6-mediated Akt phosphorylation, and the impact of anti-Tyro3 antibodies in melanoma cell lines," Biochemistry, May 2013, 52(18): 3102-18.
Dermer et al., "Another Anniversary for the War on Cancer," Bio/Technology, Mar. 1994, 12: 320.
Design of Organic Solids: Topics in Current Chemistry, 1st ed., Weber (ed)., 1998, Chapter: Crystalline Polymorphism of Organic Compounds, 46 pages.
Devi et al., "Poloxamer: A Novel Functional Molecule For Drug Delivery And Gene Therapy," J. Pharm. Sci. & Res., 2013, 5(8):159-165.
Divine et al., "AXL modulates extracellular matrix protein expression and is essential for invasion and metastasis in endometrial cancer," Oncotarget, Nov. 22, 2016, 7(47):77291-77305.
Dodonova et al., "Synthesis of 4-aryl-, 2, 4-diaryl-and 2, 4, 7-triarylpyrrolo [2, 3-d] pyrimidines by a combination of the Suzuki cross-coupling and N-arylation reactions," Tetrahedron, 2012, 68(1):329-339.
Dorai, "Aglycosylated chimeric mouse/human IgG1 antibody retains some effector function," Hybridoma., Apr. 1991, 10(2):211-217.
Dufies et al., "Mechanisms of AXL overexpression and function in Imatinib-resistant chronic myeloid leukemia cells," Oncotarget, Nov. 2011, 2(11):874-885.
Ecuador Opposition in Ecuador Application No. SENADI-2020-21655, dated May 5, 2021, 27 pages.
Encyclopedia of Biomedical Polymers and Polymeric Biomaterials, 1st ed., Mishra (ed)., Jan. 31, 2016, Chapter: Chitosan and Pluronic® F-127: Pharmaceutical Applications, 24 pages.
Eurasian Office Action in Eurasian Application No. 201892188, dated Oct. 21, 2019, 6 pages.
Eurasian Office Action in Eurasian Application No. 202190153, dated Jul. 14, 2022, 8 pages.
Eurasian Office Action in Eurasian Application No. 202292545, dated Jan. 31, 2024, 6 pages (with English Translation).
European Communication pursuant to Article 94(3) EPC in European Application No. 21196789.8, dated Mar. 2, 2023, 4 pages.
European Extended Search Report in European Application No. 21196789.8, dated Feb. 15, 2022, 7 pages.
European Office Action in European Application No. 17715620.5 dated Sep. 24, 2020, 4 pages.
European Search Report in European Application No. 23202364.8, dated Apr. 9, 2024, 13 pages.
Feneyrolles et al., "Axl kinase as a key target for oncology: focus on small molecule inhibitors," Mol Cancer Therapy, Sep. 2014, 13(9): 2141-8.
Freshney et al., "Culture of Animal Cells," A Manual of Basic Technique, Alan R. Liss, Inc., 1983, New York, p. 4.
Friend, "Phase I study of an engineered aglycosylated humanized CD3 antibody in renal transplant rejection," Transplantation, 1999, 68:1632-1637.
Gao et al., "High-throughput screening using patient-derived tumor xenografts to predict clinical trial drug response," Nat Med., 2015, 21:1318-1325.

Genbank Accession No. NP_005009 "programmed cell death protein 1 precursor [*Homo sapiens*]," Aug. 2, 2021, 4 pages.
Ghosh, "Synthesis of 4-oxazolinephenylboronic acid and heterobiaryl oxazolines via a Suzuki reaction," Journal of Chemical Research, Apr. 2009, 4:205-207.
Gibson et al., "Pharmaceutical Preformulation and Formulation," CRC Press LLC: Boca Raton, Fla., 2009, 2nd Edition, 559 pages.
Golub et al., "Molecular Classification of Cancer: Class Discovery and Class Prediction by Gene Expression Monitoring," Science, 1999, 286: 531-537.
Gould, "Salt Selection for Basic Drugs," Int J Therapeutics, 1986, 33:201-217.
Graddis et al., "Designing proteins that work using recombinant technologies," Curr Pharm Biotechnol., 2002, 3:285-297.
Graham et al., "Cloning and developmental expression analysis of the murine c-mer tyrosine kinase," Oncogene, Jun. 1995, 10(12): 2349-59.
Graham et al., "Ectopic expression of the proto-oncogene Mer in pediatric T-cell acute lymphoblastic leukemia," Clinical Cancer Research, May 1, 2006 12(9):2662-2669.
Graham et al., "The TAM family: phosphatidylserine sensing receptor tyrosine kinases gone awry in cancer," Nat. Rev. Cancer, Dec. 2014, 14(12): 769-85.
Guo et al., "Axl inhibition induces the antitumor immune response which can be further potentiated by PD-1 blockade in the mouse cancer models", Oncotarget, Oct. 27, 2017, 8(52):89761-89774.
Gustafsson et al., "Differential expression of Axl and Gas6 in renal cell carinoma reflecting tumor advancement and survival," Clin. Cancer Res., 2009, 15: 4742-4749.
Hand et al., "Comparative biological properties of a recombinant chimeric anti-carcinoma mAb and a recombinant aglycosylated variant," Cancer Immunol Immunother., 1992, 35(3):165-174.
Harmsen et al., "Properties, production, and applications of camelid single-domain antibody fragments," Appl Microbiol Biotechnol., 2007, 77(1):13-22.
Hobbs et al., "Interaction of aglycosyl immunoglobulins with the IgG Fc transport receptor from neonatal rat gut: comparison of deglycosylation by tunicamycin treatment and genetic engineering," Mol Immunol., 1992, 29:949-956.
Holland et al., "R428, a Selective Small Molecule Inhibitor of Axl Kinase, Blocks Tumor Spread and Prolongs Survival in Models of Metastatic Breast Cancer," Cancer Research, Feb. 2010, 70(4): 1544-1554.
Holliger et al., "'Diabodies': small bivalent and bispecific antibody fragments," Proc Natl Acad Sci USA., 1993, 90:6444-6448.
Hsieh et al., "The AXL receptor tyrosine kinase is associated with adverse prognosis and distant metastasis in esophageal squamous cell carcinoma," Oncotarget, Jun. 14, 2016, 7(24):36956-36970.
Huang et al., "Structural insights into the inhibited states of the Mer receptor tyrosine kinase," Journal of Structural Biology, 2009, 165: 88-96.
Hudson, et al., "High avidity scFv multimers; diabodies and triabodies," J Immunol Methods., 1999, 231:177-189.
Huston et al., "Protein engineering of antibody binding sites: recovery of specific activity in an anti-digoxin single-chain Fv analogue produced in *Escherichia coli*," Proc Natl Acad Sci USA., 1988, 85:5879-5883.
Hutterer et al., "Axl and growth arrest-specific gene 6 are frequently overexpressed in human gliomas and predict poor prognosis in patients with glioblastoma multiforme," Clinical Cancer Research, Jan. 1, 2008, 14(1):130-138.
Indian Office Action in Indian Application No. 201817040446, dated Aug. 18, 2021, 7 pages.
Indian Office Action in Indian Application No. 202017016215, dated Oct. 11, 2023, 3 pages.
Indian Office Action in Indian Application No. 202017016215, dated Oct. 4, 2021, 7 pages.
Indian Office Action in Indian Application No. 202117003850, dated Jul. 5, 2023, 3 pages.
Indian Office Action in Indian Application No. 202117003850, dated Jun. 20, 2022, 5 pages.
Indian Office Action in Indian Application No. 202117003850, dated Sep. 5, 2023, 3 pages.

(56) References Cited

OTHER PUBLICATIONS

Indonesian Office Action in Indonesian Application No. P00202002890, dated Dec. 2, 2021, 10 pages.
International Preliminary Report on Patentability in International Application No. PCT/US2016/048716, dated Nov. 2, 2016, 12 pages.
International Preliminary Report on Patentability in International Application No. PCT/US2017/024270, dated Oct. 2, 2018, 10 pages.
International Preliminary Report on Patentability in International Application No. PCT/US2018/052925, dated Mar. 31, 2020, 8 pages.
International Preliminary Report on Patentability in International Application No. PCT/US2019/039825, dated Jan. 7, 2021, 8 pages.
International Preliminary Report on Patentability in International Application No. PCT/US2021/021053, dated Sep. 15, 2022, 8 pages.
International Search Report and Written Opinion in International Application No. PCT/US2016/031625, dated Jul. 7, 2016, 11 pages.
International Search Report and Written Opinion in International Application No. PCT/US2016/046574, dated Oct. 21, 2016, 14 pages.
International Search Report and Written Opinion in International Application No. PCT/US2016/048716, dated Nov. 2, 2016, 12 pages.
International Search Report and Written Opinion in International Application No. PCT/US2017/024270, dated Jun. 14, 2017, 18 pages.
International Search Report and Written Opinion in International Application No. PCT/US2018/052925, dated Nov. 5, 2018, 14 pages.
International Search Report and Written Opinion in International Application No. PCT/US2019/039825, dated Nov. 11, 2019, 14 pages.
International Search Report in Written Opinion in International Application No. PT/US2021/021053, dated Jun. 16, 2021, 16 pages.
Isaacs et al., "Therapy with monoclonal antibodies. An in vivo model for the assessment of therapeutic potential," J Immunol., May 1992, 148(10):3062-3071.
Israel Office Action in Israeli Application No. 279,735, dated Jul. 11, 2023, 5 pages.
Israeli Office Action in Israeli Application No. 261,957, dated Oct. 28, 2020, 10 pages.
Israeli Office Action in Israeli Application No. 273,579, dated Sep. 18, 2023, 4 pages.
Israeli Office Action in Israeli Application No. 273579, dated Apr. 25, 2022, 4 pages.
Izumchenko et al. "Patient-derived xenografts effectively capture responses to oncology therapy in a heterogeneous cohort of patients with solid tumors," Ann Oncol., 2017, 28:2595-605.
Japanese Office Action in Japanese Application No. 2018-550711, dated Mar. 9, 2021, 5 pages.
Japanese Office Action in Japanese Application No. 2020-573235, dated Jun. 6, 2023, 8 pages (with Machine Translation).
Jin et al., "Patient-derived human tumour tissue xenografts in immunodeficient mice: a systematic review," Clin Transl Oncol., Jul. 2010, 12:473-480.
Johnson et al., "Relationships between drug activity in NCI preclinical in vitro and in vivo models and early clinical trials," British J. of Cancer., May 18, 2001, 84(10):1424-1431.
Kasikara, "Pan-TAM tyrosine kinase inhibitor BMS-777607 enhances anti-PD-1 mAb efficacy in a murine model of triple negative breast cancer," Cancer Research, 2019, 79(10):2669-2683.
Kaufman and Sharp, "Amplification and expression of sequences cotransfected with a modular dihydrofolate reductase complementary dna gene," Mol Biol., 1982, 159:601-621.
Keegan et al., "Preclinical Evaluation of AMG 925, a FLT3/CDK4 Kinase Inhibitor for Treating Acute Myeloid Leukemia," Molecular Cancer Therapeutics, Apr. 2014, 13(4): 880-889.
Kerekes et al., "Aurora kinase inhibitors based on the imidazo[1,2-a]pyrazine core: fluorine and deuterium incorporation improve oral absorption and exposure," J. Med. Chem., 2011, 54: 201-210.
Klimke and Ludemann, "Further evidence for a S-syn correlation in the purine (ß) ribosides: the solution conformation of two tricyclic analogs of adenosine and guanosine," Journal of Biosciences, 1979, 34C(9-10): 653-7.
Koorstra et al., "The Axl receptor tyrosine kinase confers an adverse prognostic influence in pancreatic cancer and represents a new threapeutic target," Cancer Biol. Ther., Apr. 2009, 8(7): 618-626.
Korean Office Action in Korean Application No. 10-2018-7031294, dated Oct. 27, 2021, 16 pages.
Lai and Lemke, "An extended family of protein-tyrosine kinase genes differentially expressed in the vertebrate nervous system," Neuron, May 1991, 6(5): 691-704.
Lamoyi, E., "Preparation of F(ab')2 fragments from mouse IgG of various subclasses," Methods in Enzymology, 1989, 121:652-663.
Leatherbarrow and Dwek, "The effect of aglycosylation on the binding of mouse IgG to staphylococcal protein A," FEBS Letters., 1983, 164(2):227-230.
Leatherbarrow et al., "Effector functions of a monoclonal aglycosylated mouse IgG2a: binding and activation of complement component C1 and interaction with human monocyte Fc receptor," Mol Immunol., 1985, 22(4):407-415.
Lee-Sherick et al., "Aberrant Mer receptor tyrosine kinase expression contributes to leukemogenesis in acute myeloid leukemia," Oncogene, Nov. 2013, 32(46):5359-5368.
Lei et al., "Characterization of the Erwinia carotovora pelB gene and its product pectate lyase," J Bacteriol., 1987, 169(9):4379-4383.
Lemke, "Biology of the TAM Receptors," Cold Spring Harb Perspect Biol., 2013, 5: 1-17.
Lew et al., "Differential TAM receptor-ligand-phospholipid interactions delimit differential TAM bioactivities," Elife, Sep. 2014, 3:e03385.
Li et al., "Axl as a potential therapeutic target in cancer: role of Axl in tumor growth, metastasis and angiogenesis," Oncogene, Oct. 2009, 28(39): 3442-55.
Li et al., "AXL targeting restores PD-1 blockade sensitivity of STK11/LKB1 mutant NSCLC through expansion of TCF1+ CD8 T cells," Cell Reports Medicine, 2022, 3(3):1-13.
Li et al., "Discovery of AMG 925, a FLT3 and CDK4 Dual Kinase Inhibitor with Preferential Affinity for the Activated State of FLT3," Journal of Medicinal Chemistry, 2014, 57(8): 3430-3449.
Linger et al., "Mer or Axl receptor tyrosine kinase inhibition promotes apoptosis, blocks growth and enhances chemosensitivity of human non-small cell lung cancer," Oncogene, Jul. 2013, 32(29): 3420-3431.
Linger et al., "Taking aim at Mer and Axl receptor tyrosine kinases as novel therapeutic targets in solid tumors," Expert Opin. Ther. Targets, Oct. 2010, 14(10): 1073-1090.
Linger et al., "TAM Receptor Tyrosine Kinases: Biologic Functions, Signaling, and Potential Therapeutic Targeting in Human Cancer," Adv. Cancer Research, 2008, 100: 35-83.
Lippincott Williams & Wilkins, "Remington: The Science and Practice of Pharmacy," 2005, 21st ed., 1 page, Title page.
Liu et al., "Axl Expression Stratifies Patients with Poor Prognosis after Hepatectomy for Hepatocellular Carcinoma," PLOS One, May 16, 2016, 1-13.
Liu et al., "Discovery of Novel Small Molecule Mer Kinase Inhibitors for the Treatment of Pediatric Acute Lymphoblastic Leukemia," Supporting Information, ACS Med. Chem. Lett., 2012, 53 pages.
Liu et al., "Discovery of Small Molecule Mer Kinase Inhibitors for the Treatment of Pediatric Acute Lymphoblastic Leukemia," ACS Med. Chem. Lett., 2012, 3(2): 129-134.
Liu et al., "Induction, regulation, and biologic function of Axl receptor tyrosine kinase in Kaposi sarcoma," Blood, Jul. 15, 2010, 116(2):297-305.
Liu et al., "UNC1062, a new and potent Mer inhibitor," European Journal of Medicinal Chemistry, 2013, 65: 83-93.
Lu and Lemke, "Homeostatic regulation of the immune system by receptor tyrosine kinases of the Tyro 3 family," Science, Jul. 2001, 293(5528): 306-11.

(56) References Cited

OTHER PUBLICATIONS

Lu et al., "The Effect Of A Point Mutation On The Stability Of IgG4 As Monitored By Analytical Ultracentrifugation," J. Pharmaceutical Sciences, 2008, 97:960-969.
Ludwig, et al., "Small-Molecule Inhibition of Axl Targets Tumor Immune Suppression and Enhances Chemotherapy in Pancreatic Cancer," Cancer Research, Jan. 1, 2018, 78(1):246-255.
Malaysian Office Action in Malaysian Application No. PI2020007048, dated May 31, 2024, 6 pages.
Mao et al., "Quantitation of poloxamers in pharmaceutical formulations using size exclusion chromatography and colorimetric methods," Journal of Pharmaceutical and Biomedical Analysis, 2004, 35: 1127-1142.
McMahon et al., "VEGF Receptor Signaling in Tumor Angiogenesis," The Oncologist, Feb. 14, 2000, 5(suppl 1):3-10.
Mexican Office Action in Mexican Application No. MX/a/2018/011792, dated Jul. 11, 2022, 5 pages.
Millstein et al., "Hybrid hybridomas and their use in immunohistochemistry," Nature, 1983, 305:537-539.
Mirmehrabi et al., "An approach to solvent screening for crystallization of polymorphic pharmaceuticals and fine chemicals," Journal of Pharmaceutical sciences, 2005, 94(7):1560-1576.
Mizushima et al., "pEF-BOS, a powerful mammalian expression vector," Nucleic Acids Res., 1990, 18:5322.
Mollard et al., "Design, Synthesis, and Biological Evaluation of a Series of Novel AXL Kinase Inhibitors," ACS Medicinal Chemistry Letters, 2011, 2: 907-912.
Moller et al., "Intracellular activation of interferon regulatory factor-1 by nanobodies to the multifunctional (Mf1) domain," J Biol Chem., Dec. 2010, 285(49):38348-38361.
Morissette et al., "High-throughput crystallization: polymorphs, salts, co-crystals and solvates of pharmaceutical solids," Advanced Drug Delivery Reviews, 2004, 56:257-300.
Morris et al., "An Integrated Approach to the Selection of Optimal Salt Form for a New Drug Candidate," Int J Pharm., 1994, 105:209-217.
Morrison, "Transfectomas provide novel chimeric antibodies," Science, 1985, 229:1202-1207.
Mudduluru et al., "Myeloid zinc finger 1 induces migration, invasion, and in vivo metastasis through Axl gene expression in solid cancer," Mol. Cancer Res., Feb. 2010, 8(2): 159-169.
Mulligan et al., "Synthesis of rabbit beta-globin in cultured monkey kidney cells following infection with a SV40 beta-globin recombinant genome," Nature, Jan. 1979, 277(5692):108-114.
Myers et al., "AXL inhibitors in cancer: A medicinal chemistry perspective," Journal of Medicinal Chemistry, 2015, pp. 1-53.
Myers et al., "Targeting Tyro3, Axl and MerTK (TAM receptors): implications for macrophages in the tumor microenvironment," Molecular Cancer, 2019, 18(94):1-14.
Neau "Pharmaceutical Salts," Water-Insoluble Drug Formulation, 2008, 417-435.
Nishimura et al., "Autoimmune dilated cardiomyopathy in PD-1 receptor-deficient mice," Science, 2001, 291(5502): 319-22.
Nose and Wigzell, "Biological significance of carbohydrate chains on monoclonal antibodies," 1983, Proc Natl Acad Sci USA., Nov. 1983, 80(21):6632-6636.
O'Bryan et al., "axl, a transforming gene isolated from primary human myeloid leukemia cells, encodes a novel receptor tyrosine kinase," Mol. Cell Biol., Oct. 1991, 11(10): 5016-31.
Oi et al., "Chimeric antibodies," BioTechniques, 1986, 4:214-221.
Okamoto et al., "Oligonucleotides containing 7-vinyl-7-deazaguanine as a facile strategy for expanding the functional diversity of DNA," Bioorganic & Medicinal Chemistry Letters, 2002, 12(15): 1895-1896.
Optum.com [online], "The New Age of Oncology Drugs," accessed on Jun. 21, 2023, retrieved from URL<https://www.optum.com/business/insights/pharmacy-care-services/page.hub.oncology-drug-advances.html>, 7 pages.
Paolino et al., "The E3 ligase Cbl-b and TAM receptors regulate cancer metastasis via natural killer cells," Nature, 2014, 19 pages.
Pardoll, "The blockade of immune checkpoints in cancer immunotherapy," Nat. Rev. Cancer, Mar. 2012, 12(4): 252-64.
Patani et al., "Bioisosterism: A Rational Approach in Drug Design," Chemical Reviews, 1996, 96(8):3147-3176.
Peeters et al., "TAM-ing T cells in the tumor microenvironment—implications for TAM receptor targeting," Cancer Immunology Immunotherapy, 2019, 69:237-244.
Peruvian Office Action in Peruvian Application No. 2199-2020, dated Jan. 12, 2024, 15 pages (with English Translation).
Philippine Office Action in Philippine Application No. 1/2018/502102, dated Jun. 23, 2022, 4 pages.
Philippine Office Action in Philippine Application No. 1/2018/502102, dated Sep. 14, 2021, 5 pages.
Philips et al., "Therapeutic uses of anti-PD-1 and anti-PD-L1 antibodies," International Immunology, Oct. 2014, 27(1):39-46.
Phillipines Office Action in Phillipine Application No. 1-2020-550143, dated Apr. 22, 2024, 5 pages.
Phillipines Office Action in Phillipine Application No. 1-2020-550143, dated Sep. 14, 2023, 5 pages.
Pinedo et al., "Translational Research: The Role of VEGF in Tumor Angiogenesis," The Oncologist, Feb. 22, 2000, 5(suppl 1):1-2.
Pluckthun, "Antibodies from *Escherichia coli*," The Pharmacology of Monoclonal Antibodies, 1994, 113:269-315.
Plueckthun and Skerra, "Expression of functional antibody Fv and Fab fragments in *Escherichia coli*," Methods in Enzymology, 1989, 178:497-515.
Powell et al., "Highly selective 2,4-diaminopyrimidine-5-carboxamide inhibitors of Sky kinase," Bioorganic & Medicinal Chemistry Letters, 2013, 23: 1046-1050.
Powell et al., "Novel and selective spiroindoline-based inhibitors of sky kinase," Bioorganic & Medicinal Chemistry Letters, 2012, 22: 190-193.
Powers et al., "Expression of single-chain Fv-Fc fusions in Pichia pastoris," J Immunol Methods., 2001, 251:123-135.
Raju, "Glycosylation Variations with Expression Systems and Their Impact on Biological Activity of Therapeutic Immunoglobulins," BioProcess International, Apr. 2003, 44-53.
Rankin et al., "AXL is an essential factor and therapeutic target for metastatic ovarian cancer," Cancer Research, Oct. 1, 2010, 70(19), 7570-7579.
Rao et al., "Preliminary results of a Phase 2 study of INCMGA00012 in patients with squamous carcinoma of the anal canal (SCAC) who have progressed following platinum-based chemotherapy (NCT03597295)," J. for Immunotherapy of Cancer, 2019, 7(Supplement 1):P826.
Remington's Pharmaceutical Sciences, 17th ed., Mack Publishing Company, Easton, Pa., 1985, p. 1418.
Rho et al., "MET and AXL Inhibitor NPS-1034 Exerts Efficacy against Lung Cancer Cells Resistant to EGFR Kinase Inhibitors Because of MET or AXL Activation," AARC Journals, 2013, 253-262.
Rios-Doria et al., "A Potent and Selective Dual Inhibitor of AXL and MERTK Possesses Both Immunomodulatory and Tumor-Targeted Activity", Front in Oncol., Dec. 7, 2020, 10:598477.
Rousseaux, J. et al., "Optimal conditions for the preparation of proteolytic fragments from monoclonal IgG of different rat IgG subclasses," Methods in Enzymology, 1989, 121:663-669.
Rowe et al., "Handbook of Pharmaceutical Excipients," The Pharmaceutical Press and the American Pharmaceutical Association, 2009, 6th edition, 917 pages.
Sausville et al., "Contributions of human tumor xenografts to anticancer drug development," Cancer Research, Apr. 1, 2006, 66(7):3351-3354.
Schlegel et al., "MERTK receptor tyrosine kinase is a therapeutic target in melanoma," The Journal of Clinical Investigation, May 2013, 123(5): 2257-2267.
Schlothauer et al., "Novel human IgG1 and IgG4 Fc-engineered antibodies with completely abolished immune effector functions," Protein Engineering, Design and Selection, Oct. 2016, 29(10):457-466.
Schroeder et al., "Discovery of N-(4-(2-Amino-3-chloropyridin-4-yloxy)-3-fluorophenyl)-4-ethoxy-1-(4-fluorophenyl)-2-oxo-1,2-dihydropyridine-3- carboxamide (BMS-777607), a Selective and

(56) References Cited

OTHER PUBLICATIONS

Orally Efficacious Inhibitor of the Met Kinase Superfamily," J. Med. Chem., 2009, 52: 1251-1254.
Shibata et al., "Axl receptor blockade ameliorates pulmonary pathology resulting from primary viral infection and viral exacerbation of asthma," The Journal of Immunology, 2014, 192: 3569-3581.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem., 2001, 276(9):6591-6604.
Shields et al., "Lack of fucose on human IgG1 N-linked oligosaccharide improves binding to human Fcgamma RIII and antibody-dependent cellular toxicity," J Biol Chem., 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., 2003, 278(5):3466-3473.
Singer et al., "Photochromism of Diarylethene-Functionalized 7-Deazaguanosines," European Journal of Organic Chemistry, 2013, 14: 2766-2769.
Skardziute, "Optical study of the formation of pyrrolo[2,3-d]pyrimidine-based fluorescent nanoaggregates," Tetrahedron, 2013, 69(46):9566-9572.
Storey et al., "Solid State Characterization of Pharmaceuticals," 2011, 170 pages.
Strassmaier and Karpen, "Novel N7- and N1-Substituted cGMP Derivatives Are Potent Activators of Cyclic Nucleotide-Gated Channels," Journal of Medicinal Chemistry, Aug. 2007, 50: 4186-4194.
Suarez et al., "Inhibitors of the TAM subfamily of tyrosine kinsases: Synthesis and biological evaluation," European Journal of Medicinal Chemistry, 2013, 61: 2-25.
Swarbrick et al., "Salt Forms of Drugs and Absorption," Encyclopedia of Pharmaceutical Technology, 1996, 13:453-499.
Tai et al., "Axl promotes cell invasion by inducing MMP-9 activity through activation of NF-kappaB and Brg-1," Oncogene, Jul. 2008, 27(29): 4044-55.
Taiwanese Office Action in Taiwanese Application No. 108122789, dated Mar. 9, 2023, 8 pages (with English translation).
Tao et al., "Studies of aglycosylated chimeric mouse-human IgG. Role of carbohydrate in the structure and effector functions mediated by the human IgG constant region," J Immunol., Oct. 15, 1989, 143(8):2595-2601 (Abstract Only).
Tempest et al., "Reshaping a human monoclonal antibody to inhibit human respiratory syncytial virus infection in vivo," Biotechnology, 1991, 9:266-271.
Tomlinson et al., "The repertoire of human germline VH sequences reveals about fifty groups of VH segments with different hypervariable loops" J Mol Biol., 1992, 227(3):776-798.
Tomlinson et al., "The structural repertoire of the human V kappa domain," EMBO J., 1995, 14:4628-4638.
Traore et al., "New aminopyrimidine derivatives as inhibitors of the TAM family," European Journal of Medicinal Chemistry, 2013, 70: 789-801.
Tumkevicius, "Pyrrolo [2, 3-d] pyrimidine-Core-Extended π-Systems: Synthesisof 2, 4, 7-Triarylpyrrolo [2, 3-d] pyrimidines," Synlett, 2011, 12:1705-1708.
Tumkevicius, "Synthesis and photophysical properties of oligoarylenes with a pyrrolo [2, 3-d] pyrimidine core," Tetrahedron Letters (2010), 51(30), 3902-3906.
Ukraine Office Action in Ukraine Application No. a201810566, dated Dec. 15, 2020, 8 pages.
Ukraine Office Action in Ukraine Application No. a202002558, dated Feb. 18, 2022, 8 pages.
Ukrainian Office Action in Ukrainian Application No. a202100313, dated Feb. 8, 2024, 8 pages (with English Translation).
Umana et al., "Engineered glycoforms of an antineuroblastoma IgG1 with optimized antibody-dependent cellular cytotoxic activity," Nat Biotechnol., Feb. 1999, 17(2):176-180.
United Arab Emirates Office Action in United Arab Emirates Application No. 2020-6000459, dated Oct. 30, 2023, 9 pages.
Urbonas et al., "A Novel Highly Site-Selective Synthesis of 2,4,7-Triarylpyrrolo[2,3-d]pyrimidines by a Combination of Palladium(0)-, Nickel(0)-, and Copper(I)-Catalyzed Cross-Coupling Reactions," Synlett, 2013, 24(11):1383-1386.
Urlaub and Chasin, "Isolation of Chinese hamster cell mutants deficient in dihydrofolate reductase activity," Proc Natl Acad Sci USA., 1980, 77:4216-4220.
Waizeneggar et al., "Role of Growth arrest-specific gene 6-Mer axis in multiple myeloma," Leukemia, 2015, 29: 696-704.
Walker et al., "Aglycosylation of human IgG1 and IgG3 monoclonal antibodies can eliminate recognition by human cells expressing Fc gamma RI and/or Fc gamma RII receptors," Biochem J., 1989, 259:347-353.
Wang et al., "Mer receptor tyrosine kinase promotes invasion and survival in glioblastoma multiforme," Oncogene, Feb. 2013, 32(7): 872-882.
Ward and Ghetie, "The effector functions of immunoglobulins: implications for therapy," Therapeutic Immunology, 1995, 2:77-94.
Ward et al., "Binding activities of a repertoire of single immunoglobulin variable domains secreted from *Escherichia coli*," Nature, Oct. 12, 1989, 341(6242):544-546.
Wright & Morrison, "Effect of glycosylation on antibody function: implications for genetic engineering," Tibtech., 1997, 15(1):26-32.
Wu et al., "Multisubstituted quinoxalines and pyrido[2,3-d]pyrimidines: Synthesis and SAR study as tyrosine kinase c-Met inhibitors," Bioorganic & Medicinal Chemistry Letters, 2012, 22: 6368-6372.
Xu et al., "Design, synthesis and biological evaluation of deuterated nintedanib for improving pharmacokinetic properties," J. Label Compd. Radiopharm., 2015, 58: 308-312.
Yamazoe et al., "Mechanism of formation and structural characterization of DNA adducts derived from peroxidative activation of benzidine," Carcinogenesis, Sep. 1988, 9(9): 1635-41.
Yokoyama et al., "Immuno-Oncological Efficacy of RXDX-106, a Novel Small Molecule Inhibitor of TAM (TYRO3, AXL, MER) family of kinases," 2019, 79(8):1996-2008.
Zhang et al., "Activation of the AXL kinase causes resistance to EGFR-targeted therapy in lung cancer," Nat. Genet., 2012, 44(8): 852-860.
Zhang et al., "Discovery of Mer Specific Tyrosine Kinase Inhibitors for the Treatment and Prevention of Thrombosis," Journal of Medicinal Chemistry, 2013, 56: 9693-9700.
Zhang et al., "Discovery of novel type II c-Met inhibitors based on BMS-777607," European Journal of Medicinal Chemistry, 2014, 80: 254-266.
Zhang et al., "Knockdown of AXL receptor tyrosine kinase in osteosarcoma cells leads to decreased proliferation and increased apoptosis," Int. J. Immunopathol. Pharmacol., Jan.-Mar. 2013, 26(1):179-188.
Zhang et al., "Pseudo-Cyclization through Intramolecular Hydrogen Bond Enables Discovery of Pyridine Substituted Pyrimidines as New Mer Kinase Inhibitors," Journal of Medicinal Chemistry, 2013, 56: 6983-9692.
Zhang et al., "UNC20205, a Potent and Orally Bioavailable MER/FLT3 Dual Inhibitor," Journal of Medicinal Chemistry, 2014, 57: 7031-7041.
Zhao et al., "Discovery of novel Bruton's tyrosine kinase (BTK) inhibitors bearing a pyrrolo [2, 3-d] pyrimidine scaffold," Bioorganic & Medicinal Chemistry, Feb. 2015, 23(4):891-901.
Zhou et al., "Synthesis and evaluation of Janus type nucleosides as potential HCV NS5B polymerase inhibitors," Bioorganic & Medicinal Chemistry Letters, Jun. 2013, 23: 3385-3388.

FORMULATIONS OF AN AXL/MER INHIBITOR

SEQUENCE LISTING

This application contains a Sequence Listing that has been submitted electronically as an XML file named "20443-0567003.XML." The XML file, created on Jan. 31, 2024, is 1,887 bytes in size. The material in the XML file is hereby incorporated by reference in its entirety.

FIELD

This application relates to pharmaceutical formulations and solid dosage forms of an AXL/MER inhibitor, or a pharmaceutically acceptable salt, solvate, or hydrate thereof, including methods of preparation thereof, which are useful in the treatment of AXL/MER mediated diseases such as cancer.

BACKGROUND

Receptor tyrosine kinases (RTKs) are cell surface proteins that transmit signals from the extracellular environment to the cell cytoplasm and nucleus to regulate cellular events such as survival, growth, proliferation, differentiation, adhesion and migration.

The TAM subfamily consists of three RTKs including Tyro3, AXL and MER (Graham et al., 2014, Nature Reviews Cancer 14, 769-785; Linger et al., 2008, Advances in Cancer Research 100, 35-83). TAM kinases are characterized by an extracellular ligand binding domain consisting of two immunoglobulin-like domains and two fibronectin type III domains. Two ligands, growth arrest specific 6 (GAS6) and protein S (PROS1), have been identified for TAM kinases. GAS6 can bind to and activate all three TAM kinases, while PROS1 is a ligand for Mer and Tyro3 (Graham et al., 2014, Nature Reviews Cancer 14, 769-785).

AXL (also known as UFO, ARK, JTK11 and TYRO7) was originally identified as a transforming gene from DNA of patients with chronic myelogenous leukemia (O'Bryan et al., 1991, Mol Cell Biol 11, 5016-5031; Graham et al., 2014, Nature Reviews Cancer 14, 769-785; Linger et al., 2008, Advances in Cancer Research 100, 35-83). GAS6 binds to AXL and induces subsequent auto-phosphorylation and activation of AXL tyrosine kinase. AXL activates several downstream signaling pathways including PI3K-Akt, Raf-MAPK, PLC-PKC (Feneyrolles et al., 2014, Molecular Cancer Therapeutics/3, 2141-2148; Linger et al., 2008, Advances in Cancer Research 100, 35-83).

MER (also known as MERTK, EYK, RYK, RP38, NYK and TYRO12) was originally identified as a phospho-protein from a lymphoblastoid expression library (Graham et al., 1995, Oncogene 10, 2349-2359; Graham et al., 2014, Nature Reviews Cancer 14, 769-785; Linger et al., 2008, Advances in Cancer Research 100, 35-83). Both GAS6 and PROS1 can bind to Mer and induce the phosphorylation and activation of Mer kinase (Lew et al., 2014). Like AXL, MER activation also conveys downstream signaling pathways including PI3K-Akt and Raf-MAPK (Linger et al., 2008, Advances in Cancer Research 100, 35-83).

TYRO3 (also known as DTK, SKY, RSE, BRT, TIF, ETK2) was originally identified through a PCR-based cloning study (Lai et al., Neuron 6, 691-70, 1991; Graham et al., 2014, Nature Reviews Cancer 14, 769-785; Linger et al., 2008, Advances in Cancer Research 100, 35-83). Both ligands, GAS6 and PROS1, can bind to and activate TYRO3. Although the signaling pathways downstream of TYRO3 activation are the least studied among TAM RTKs, it appears that both PI3K-Akt and Raf-MAPK pathways are involved (Linger et al., 2008, Advances in Cancer Research 100, 35-83). AXL, MER and TYRO3 are found to be over-expressed in cancer cells.

Accordingly, there is a need for compounds and methods of use thereof for the modulation of AXL/MER kinases in the treatment of cancer.

SUMMARY

The present invention is directed to, inter alia, a pharmaceutical formulation comprising N-(4-(4-amino-7-(1-isobutyrylpiperidin-4-yl)pyrrolo[2,1-f][1,2,4]triazin-5-yl)phenyl)-1-isopropyl-2,4-dioxo-3-(pyridin-2-yl)-1,2,3,4-tetrahydropyrimidine-5-carboxamide (Compound I), or a pharmaceutically acceptable salt, solvate or hydrate thereof, an organic acid, and a surfactant.

The present invention is further directed to a dosage form comprising a pharmaceutical formulation provided herein.

The present invention is further directed to a method of treating a disease associated with AXL/MER activity comprising administering to a patient in need thereof a therapeutically effective amount of a pharmaceutical formulation or a dosage form provided herein.

DETAILED DESCRIPTION

Figure 1:
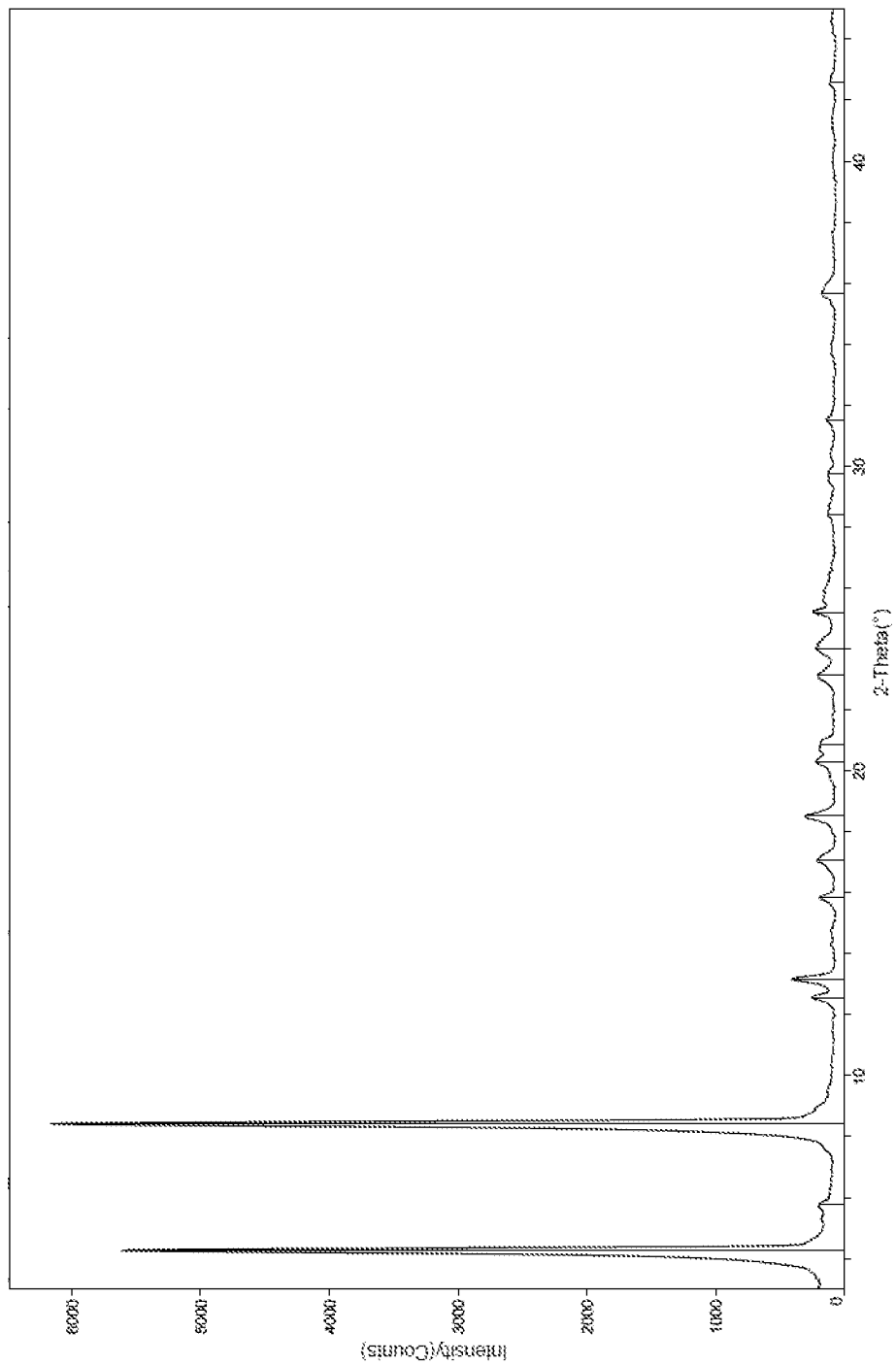
FIG. 1 shows an XRPD pattern representative of Compound I maleic acid salt.

The present invention relates to pharmaceutical compositions (or formulations) and dosage forms of Compound I, or a pharmaceutically acceptable salt (e.g., Compound 1 maleic acid salt), hydrate or solvate thereof, having improved properties such as bioavailability. In particular, the formulations and dosage forms of the present invention help increase the bioavailability of Compound I (e.g., Compound I maleate). Inclusion of an organic acid, such as citric acid, and a surfactant such as a poloxamer (e.g., poloxamer 407) can provide increased bioavailability.

Formulations

The present invention provides, inter alia, a pharmaceutical formulation in solid oral dosage form comprising:

(a) N-(4-(4-amino-7-(1-isobutyrylpiperidin-4-yl)pyrrolo[2,1-f][1,2,4]triazin-5-yl)phenyl)-1-isopropyl-2,4-dioxo-3-(pyridin-2-yl)-1,2,3,4-tetrahydropyrimidine-5-carboxamide (Compound I), or a pharmaceutically acceptable salt (e.g., Compound 1 maleate), solvate or hydrate thereof;

(b) an organic acid; and (c) a surfactant.

Compound I is an AXL/MER inhibitor and refers to N-(4-(4-amino-7-(1-isobutyrylpiperidin-4-yl)pyrrolo[2,1-f][1,2,4]triazin-5-yl)phenyl)-1-isopropyl-2,4-dioxo-3-(pyridin-2-yl)-1,2,3,4-tetrahydropyrimidine-5-carboxamide having the formula:

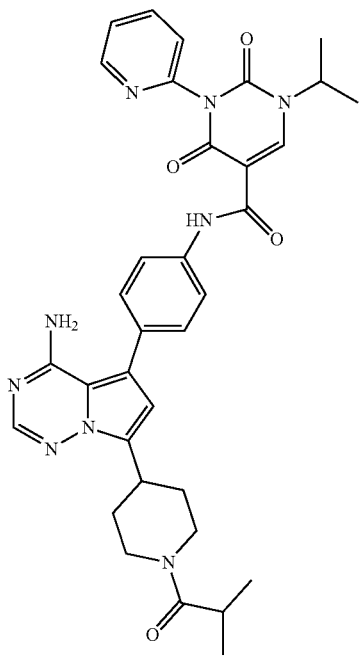

Compound I

Compound I maleic acid salt refers to N-(4-(4-amino-7-(1-isobutyrylpiperidin-4-yl)pyrrolo[2,1-f][1,2,4]triazin-5-yl)phenyl)-1-isopropyl-2,4-dioxo-3-(pyridin-2-yl)-1,2,3,4-tetrahydropyrimidine-5-carboxamide maleate, which is also referred to as "Compound I maleic acid," or "Compound I maleate." The present disclosure also includes other salts of Compound I. Examples of such salts include, e.g., sulfuric acid salt (e.g., hemi-sulfuric acid salt), phosphoric acid salt, hydrochloric acid salt, salicylic acid salt, methanesulfonic acid salt (i.e., mesylate salt), ethanesulfonic acid salt (i.e., esylate salt), benzenesulfonic acid salt (i.e., besylate salt), and p-toluenesulfonic acid salt (e.g., tosylate salt).

Compound I can be prepared according to the procedures in U.S. Pat. No. 9,981,975. See e.g., Example 83. Compound I maleic acid salt and various crystalline forms can be prepared according to the procedures in U.S. Provisional Application 62/564,070. See also e.g., examples provided herein.

In some embodiments, Compound I, or a pharmaceutically acceptable salt, solvate, or hydrate thereof, used herein is in crystalline form. In some embodiments, Compound I, or a pharmaceutically acceptable salt, solvate, or hydrate thereof used herein is non-crystalline. In other embodiments, Compound I, or a pharmaceutically acceptable salt, solvate, or hydrate thereof used herein is a hydrate. In some embodiments, Compound I, or a pharmaceutically acceptable salt, solvate, or hydrate thereof used herein is a solvate. In some embodiments, Compound I, or a pharmaceutically acceptable salt, solvate, or hydrate thereof, used herein is anhydrous.

In some embodiments, Compound I maleate used herein is in crystalline form. In some embodiments, Compound I maleate used herein is non-crystalline. In other embodiments, Compound I maleate used herein is a hydrate. In some embodiments, Compound I maleate used herein is a solvate. In some embodiments, Compound I maleate used herein is anhydrous.

In some embodiments, the present invention provides a pharmaceutical formulation comprising:

(a) Compound I, or a pharmaceutically acceptable salt, solvate, or hydrate thereof,
(b) an organic acid, and
(c) a surfactant.

In certain embodiments, the pharmaceutical formulation provided herein further includes a diluent. In certain embodiments, the pharmaceutical formulation provided herein further includes a lubricant. In some embodiments, the pharmaceutical formulation provided herein can further include a disintegrant.

In some embodiments, the pharmaceutical formulation comprises about 1 wt % to about 20 wt % of Compound I, or a pharmaceutically acceptable salt, solvate, or hydrate thereof. In some embodiments, the pharmaceutical formulation comprises about 2 wt % to about 15 wt % of Compound I, or a pharmaceutically acceptable salt, solvate, or hydrate thereof. In some embodiments, the pharmaceutical formulation comprises about 3 wt % to about 12 wt % of Compound I, or a pharmaceutically acceptable salt, solvate, or hydrate thereof. In some embodiments, the pharmaceutical formulation comprises about 5 wt % to about 10 wt % of Compound I, or a pharmaceutically acceptable salt, solvate, or hydrate thereof. In some embodiments, the pharmaceutical formulation comprises about 3 wt % to about 8 wt % of Compound I, or a pharmaceutically acceptable salt, solvate, or hydrate thereof. In some embodiments, the pharmaceutical formulation comprises about 2 wt % to about 6 wt % of Compound I, or a pharmaceutically acceptable salt, solvate, or hydrate thereof. In some embodiments, the pharmaceutical formulation comprises about 3 wt %, about 4 wt %, about 5 wt %, about 6 wt %, about 7 wt %, about 8 wt %, about 9 wt %, about 10 wt %, about 11 wt %, or about 12 wt % of Compound I, or a pharmaceutically acceptable salt, solvate, or hydrate thereof. In some embodiments, the pharmaceutical formulation comprises about 3 wt % of Compound I maleate. In some embodiments, the pharmaceutical formulation comprises about 12 wt % of Compound I, or a pharmaceutically acceptable salt, solvate, or hydrate thereof.

In some embodiments, the pharmaceutical formulation comprises about 1 wt % to about 20 wt % of Compound I maleate. In some embodiments, the pharmaceutical formulation comprises about 2 wt % to about 15 wt % of Compound I maleate. In some embodiments, the pharmaceutical formulation comprises about 3 wt % to about 12 wt % of Compound I maleate. In some embodiments, the pharmaceutical formulation comprises about 5 wt % to about 10 wt % of Compound I maleate. In some embodiments, the pharmaceutical formulation comprises about 3 wt % to about 8 wt % of Compound I maleate. In some embodiments, the pharmaceutical formulation comprises about 2 wt % to about 6 wt % of Compound I maleate. In some embodiments, the pharmaceutical formulation comprises about 3 wt %, about 4 wt %, about 5 wt %, about 6 wt %, about 7 wt %, about 8 wt %, about 9 wt %, about 10 wt %, about 11 wt %, or about 12 wt % of Compound I maleate. In some embodiments, the pharmaceutical formulation comprises about 3 wt % of Compound I maleate. In some embodiments, the pharmaceutical formulation comprises about 4 wt % of Compound I maleate. In some embodiments, the pharmaceutical formulation comprises about 7 wt % of Compound I maleate. In some embodiments, the pharmaceutical formulation comprises about 12 wt % of Compound I maleate.

The weight percentage and amount of Compound I described herein are calculated based on the free base of Compound I unless specified otherwise.

The surfactant present in certain formulations of the invention helps increase bioavailability of Compound I, or a pharmaceutically acceptable salt (e.g., Compound I maleate), solvate, or hydrate thereof. The term "surfactants" refers to compounds that lower the surface tension between two liquids, or between a liquid and a solid. In some embodiments, surfactants can also have other functions such as detergents, wetting agents, emulsifiers, foaming agents, and dispersants. Exemplary surfactants include, but are not limited to, poloxamers. Examples of poloxamers are poloxamer 407, poloxamer 338, poloxamer 237, and poloxamer 188. In one embodiment, the poloxamer is poloxamer 188. In one embodiment, the poloxamer is poloxamer 407. Poloxamer is a polyethylene-propylene glycol copolymer (known trade names are Supronic, Pluronic or Tetronic) that has thermoreversible property and sol-gel transition property that can help drug release. For example, poloxamer exhibits in a sol state at less than room temperature and converts to a gel state at body temperature (37.2° C.), which can modify drug release characteristics (D. Ramya Devi et al, J. Pharm. Sci. & Res. Vol. 5(8), 2013, 159-165; Y. Mao et al. Journal of Pharmaceutical and Biomedical Analysis 35 (2004) 1127-1142).

In some embodiments, the surfactant used in the formulations is poloxamer 407. It is unexpected that poloxamer 407 increases the bioavailability of Compound I maleate because, among other things, solubility studies showed that surfactant sodium lauryl sulfate (SLS) increased the solubility of Compound I maleate compared to poloxamer 407, but the bioavailability of a formulation comprising SLS is lower than that of a formulation comprising a poloxamer. See examples provided herein.

The surfactant in the formulation can be from about 1 wt % to about 20 wt %. The surfactant in the formulation can be from about 5 wt % to about 15 wt %. The surfactant in the formulation can be from about 1 wt % to about 10 wt %. The surfactant in the formulation can be from about 5 wt % to about 10 wt %. For example, the surfactant in the formulation can be about 1, about 2, about 3, about 4, about 5, about 6, about 7, about 8, about 9, about 10, about 15, or about 20 by wt %. In some embodiments, the surfactant in the formulation is about 5 wt %. In some embodiments, the surfactant in the formulation is about 10 wt %.

In some embodiments, the surfactant is poloxamer 407. The poloxamer (e.g., poloxamer 407) in the formulation can be from about 1 wt % to about 20 wt %. The poloxamer (e.g., poloxamer 407) in the formulation can be from about 1 wt % to about 10 wt %. The poloxamer (e.g., poloxamer 407) in the formulation can be from about 5 wt % to about 15 wt %. The poloxamer (e.g., poloxamer 407) in the formulation can be from about 5 wt % to about 10 wt %. For example, the poloxamer (e.g., poloxamer 407) in the formulation can be about 1, about 2, about 3, about 4, about 5, about 6, about 7, about 8, about 9, about 10, about 15, or about 20 by wt %. In some embodiments, the poloxamer (e.g., poloxamer 407) in the formulation is about 5 wt %. In some embodiments, the poloxamer (e.g., poloxamer 407) in the formulation is about 10 wt %.

The formulations of the invention include an organic acid, which can increase the bioavailability of Compound I. The term "organic acid" refers to an organic compound with acidic properties. In some embodiments, the organic acid is $C_{1-6}$ alkyl, $C_{2-6}$ alkenyl, or 5-6 membered heterocycloalkyl, each substituted with one or more acidic groups (e.g., 1, 2, or 3 carboxylic acid, alcohol, or sulfonic acid groups), wherein the 5-6 membered heterocycloalkyl is optionally substituted with a $C_{1-6}$ alkyl group that is optionally substituted with one or more acidic groups (e.g., 1, 2, 3, or 4 carboxylic acid, alcohol, or sulfonic acid groups). The organic acid can be a $C_{1-6}$ alkyl or $C_{2-6}$ alkenyl substituted with one or more acidic groups (e.g., 1, 2, 3, or 4 carboxylic acid, alcohol, or sulfonic acid groups). In some embodiments, the organic acid is a $C_{1-6}$ alkyl or $C_{2-6}$ alkenyl substituted with 1, 2, or 3 carboxylic acid groups and substituted with 0, 1, or 2 alcohol groups. In some embodiments, the organic acid is 5-6 membered heterocycloalkyl substituted with one or more acidic groups (e.g., 1, 2, or 3 carboxylic acid, alcohol, or sulfonic acid groups) and optionally substituted with a $C_{1-6}$ alkyl, wherein the $C_{1-6}$ alkyl is optionally substituted with one or more acidic groups (e.g., 1, 2, or 3 carboxylic acid, alcohol, or sulfonic acid groups). Exemplary organic acids include, but are not limited to, citric acid, ascorbic acid, fumaric acid, malic acid, sorbic acid, tartaric acid and hydrates or solvates thereof. The organic acid in the formulation can be from about 1 wt % and to about 50 wt %. The organic acid in the formulation can be from about 5 wt % to about 40 wt %. The organic acid in the formulation can be from about 5 wt % to about 30 wt %. The organic acid in the formulation can be from about 5 wt % to about 20 wt %. The organic acid in the formulation can be from about 10 wt % to about 20 wt %. For example, the organic acid in the formulation can be about 1, 2, 3, 4, 5, 6, 7, 8, 9, 10, 15, 20, 25, 30, 35, 40, 45 or 50% by weight. In some embodiments, the organic acid in the formation is about 10 wt %. In some embodiments, the organic acid in the formation is about 20 wt %.

In some embodiments, the organic acid is citric acid. In some embodiments, the citric acid is citric acid monohydrate. The citric acid in the formulation can be from about 1 wt % and to about 50 wt %. The citric acid in the formulation can be from about 5 wt % to about 40 wt %. The citric acid in the formulation can be from about 5 wt % to about 30 wt %. The citric acid in the formulation can be from about 5 wt % to about 20 wt %. The citric acid in the formulation can be from about 10 wt % to about 20 wt %. For example, the citric acid in the formulation can be about 1, 2, 3, 4, 5, 6, 7, 8, 9, 10, 15, 20, 25, 30, 35, 40, 45 or 50% by weight. In some embodiments, the citric acid in the formation is about 10 wt %. In some embodiments, the citric acid in the formation is about 20 wt %.

The pharmaceutical formulations provided herein can further include a diluent. As used herein, the term "diluent" refers to a compound that can diluting a composition. Diluent can also be referred to as a filler, dilutant or thinner. Exemplary diluents include, but are not limited to, lactose, lactose monohydrate, spray-dried monohydrate lactose, lactose-316 Fast Flo®, mannitol, microcrystalline cellulose, acidified cellulose, starch 1500, prosolve MCC, and colloidal silica. In certain instances, the diluent is mannitol. The diluent in the formulation can be from about 40 wt % to about 90 wt %. The diluent in the formulation can be from about 50 wt % to about 80 wt %. The diluent in the formulation can be from about 50 wt % to about 75 wt %. The diluent in the formulation can be from about 70 wt % to about 80 wt %. The diluent in the formulation can be from about 72 wt % to about 77 wt %. For example, the diluent in the formulation can be about 40, about 45, about 50, about 55, about 60, about 65, about 70, about 75, about 80, about 85, or about 90% by weight. In some embodiments, the diluent in the formulation is about 50 wt %. In some embodiments, the diluent in the formulation is about 75 wt %. In some embodiments, the diluent in the formulation is about 73 wt %. In some embodiments, the diluent in the formulation is about 76 wt %.

In some embodiments, the formulations of the invention include a disintegrant. As used herein, the term "disintegrant" refers to a compound that can cause a formulation (e.g., capsules or tablets) to disintegrate and release its drug substance, on contact with moisture. Disintegrants can facilitate, e.g., a capsule, to break up after oral administration. Disintegrants can be present in an amount of about 1 wt % to about 10 wt %. The disintegrant in the formulation can be about 2 wt % to about 5 wt %. The disintegrant in the formulation can be about 2 wt % to about 3 wt %. The disintegrant in the formulation can be about 2.5 wt %. Non-limiting examples of disintegrants include croscarmellose sodium, crospovidone, starch, cellulose, and low substituted hydroxypropyl cellulose. In some embodiments, the disintegrant is crospovidone.

In some embodiments, the formulations of the invention include a lubricant. As used herein, the term "lubricant" refers to a compound, e.g., an organic compound that can reduce friction among the substances in a formulation. Lubricants can be present in the formulations in an amount of about 1 wt % to about 5 wt %. In some embodiments, the lubricant is present in an amount of about 2 wt %. Non-limiting examples of lubricants include magnesium stearate, stearic acid (stearin), hydrogenated oil, polyethylene glycol, sodium stearyl fumarate, and glyceryl behenate. In some embodiments, the lubricant is sodium stearyl fumarate or stearic acid. In some embodiments, the lubricant is stearic acid.

In some embodiments, the formulations provided herein include a glidant. As used herein, the term "glidant" refers to a compound that can improve flowability of a mixture, e.g., a powder mixture in a capsule. Glidants can be present in the formulations in an amount of about 0.1 wt % to about 5 wt %. In some embodiments, the glidant in the formulation is about 0.5 wt % to about 1 wt %. In some embodiments, the glidant in the formulation is about 0.1 wt % to about 1 wt %. In some embodiments, the glidant in the formulation is about 0.5 wt %. Non-limiting examples of glidants include talc, colloidal silica (colloidal silicon dioxide), and cornstarch. In some embodiments, the glidant is colloidal silica.

In some embodiments, where for example the formulations and dosage forms of the invention are intended for sustained-release dosage forms, a sustained-release matrix former can be included. Example sustained-release matrix formers include cellulosic ethers such as hydroxypropyl methylcellulose (HPMC, hypromellose) which is a high viscosity polymer. The sustained-release dosage forms of the invention can include, for example, about 10 to about 30%, about 15 to about 25%, or about 18 to about 24% by weight of a sustained-release matrix former.

In some embodiments, provided herein is a pharmaceutical formulation comprising:
(a) Compound I, or a pharmaceutically acceptable salt, solvate, or hydrate thereof;
(b) citric acid; and
(c) a poloxamer.

In some embodiments, provided herein is a pharmaceutical formulation comprising:
(a) about 2 wt % to about 15 wt % of Compound I, or a pharmaceutically acceptable salt, solvate, or hydrate thereof;
(b) about 5 wt % to about 30 wt % of citric acid; and
(c) about 5 wt % to about 15 wt % a poloxamer.

In some embodiments, provided herein is a pharmaceutical formulation comprising:
(a) about 2 wt % to about 15 wt % of N-(4-(4-amino-7-(1-isobutyrylpiperidin-4-yl)pyrrolo[2,1-f][1,2,4]triazin-5-yl)phenyl)-1-isopropyl-2,4-dioxo-3-(pyridin-2-yl)-1,2,3,4-tetrahydropyrimidine-5-carboxamide (Compound I), or a pharmaceutically acceptable salt, solvate or hydrate thereof;
(b) about 5 wt % to about 30 wt % of citric acid; and
(c) about 1 wt % to about 10 wt % a poloxamer.

In some embodiments, provided herein is a pharmaceutical formulation comprising:
(a) Compound I, or a pharmaceutically acceptable salt, solvate, or hydrate thereof;
(b) citric acid acid;
(c) a poloxamer (e.g., poloxamer 407); and
(d) a diluent (e.g., mannitol).

In some embodiments, provided herein is a pharmaceutical formulation comprising:
(a) about 2 wt % to about 15 wt % of Compound I, or a pharmaceutically acceptable salt, solvate, or hydrate thereof;
(b) about 5 wt % to about 30 wt % of citric acid;
(c) about 5 wt % to about 15 wt % poloxamer (e.g., poloxamer 407); and
(d) about 50 wt % to about 80 wt % diluent (e.g., mannitol).

In some embodiments, provided herein is a pharmaceutical formulation comprising:
(a) Compound I, or a pharmaceutically acceptable salt, solvate, or hydrate thereof;
(b) citric acid acid;
(c) a poloxamer (e.g., poloxamer 407);
(d) a diluent (e.g., mannitol); and
(e) a lubricant (e.g., stearic acid).

In some embodiments, provided herein is a pharmaceutical formulation comprising:
(a) about 2 wt % to about 15 wt % of Compound I, or a pharmaceutically acceptable salt, solvate, or hydrate thereof;
(b) about 5 wt % to about 30 wt % of citric acid;
(c) about 5 wt % to about 15 wt % poloxamer (e.g., poloxamer 407);
(d) about 50 wt % to about 80 wt % diluent (e.g., mannitol); and
(e) about 1 wt % to about 5 wt % lubricant (e.g., stearic acid).

In some embodiments, provided herein is a pharmaceutical formulation comprising:
(a) Compound I, or a pharmaceutically acceptable salt, solvate, or hydrate thereof;
(b) citric acid acid;
(c) a poloxamer (e.g., poloxamer 407);
(d) a diluent (e.g., mannitol);
(e) a lubricant (e.g., stearic acid); and
(f) a disintegrant (e.g., crospovidone).

In some embodiments, provided herein is a pharmaceutical formulation comprising:
(a) about 2 wt % to about 15 wt % of Compound I, or a pharmaceutically acceptable salt, solvate, or hydrate thereof;
(b) about 5 wt % to about 30 wt % of citric acid;
(c) about 5 wt % to about 15 wt % poloxamer (e.g., poloxamer 407);
(d) about 50 wt % to about 80 wt % diluent (e.g., mannitol);
(e) about 1 wt % to about 5 wt % lubricant (e.g., stearic acid); and
(f) about 2 wt % to about 5 wt % disintegrant (e.g., crospovidone).

In some embodiments, provided herein is a pharmaceutical formulation comprising:
(a) about 2 wt % to about 15 wt % of Compound I, or a pharmaceutically acceptable salt, solvate, or hydrate thereof;
(b) about 5 wt % to about 30 wt % of citric acid;
(c) about 1 wt % to about 10 wt % poloxamer (e.g., poloxamer 407);
(d) about 50 wt % to about 80 wt % diluent (e.g., mannitol);
(e) about 1 wt % to about 5 wt % lubricant (e.g., stearic acid); and
(f) about 2 wt % to about 5 wt % disintegrant (e.g., crospovidone).

In some embodiments, provided herein is a pharmaceutical formulation comprising:
(a) about 2 wt % to about 15 wt % of Compound I, or a pharmaceutically acceptable salt, solvate, or hydrate thereof;
(b) about 5 wt % to about 30 wt % of citric acid;
(c) about 5 wt % to about 15 wt % poloxamer 407;
(d) about 50 wt % to about 80 wt % mannitol;
(e) about 1 wt % to about 5 wt % stearic acid; and
(f) about 2 wt % to about 5 wt % crospovidone.

In some embodiments, provided herein is a pharmaceutical formulation comprising:
(a) about 2 wt % to about 15 wt % of N-(4-(4-amino-7-(1-isobutyrylpiperidin-4-yl)pyrrolo[2,1-f][1,2,4]triazin-5-yl)phenyl)-1-isopropyl-2,4-dioxo-3-(pyridin-2-yl)-1,2,3,4-tetrahydropyrimidine-5-carboxamide (Compound I), or a pharmaceutically acceptable salt, solvate or hydrate thereof;
(b) about 5 wt % to about 30 wt % of citric acid;
(c) about 1 wt % to about 10 wt % poloxamer 407;
(d) about 50 wt % to about 80 wt % mannitol;
(e) about 1 wt % to about 5 wt % stearic acid; and
(f) about 2 wt % to about 5 wt % crospovidone.

In some embodiments, provided herein is a pharmaceutical formulation comprising:
(a) about 12 wt % of Compound I, or a pharmaceutically acceptable salt, solvate, or hydrate thereof;
(b) about 20 wt % of citric acid; and
(c) about 10 wt % poloxamer 407.

In some embodiments, provided herein is a pharmaceutical formulation comprising:
(a) about 12 wt % of Compound I, or a pharmaceutically acceptable salt, solvate, or hydrate thereof;
(b) about 20 wt % of citric acid;
(c) about 10 wt % poloxamer 407;
(d) about 50 wt % mannitol;
(e) about 2 wt % stearic acid; and
(f) about 5 wt % crospovidone.

In some embodiments, provided herein is a pharmaceutical formulation comprising:
(a) about 3 wt % of Compound I, or a pharmaceutically acceptable salt, solvate, or hydrate thereof;
(b) about 20 wt % of citric acid; and
(c) about 10 wt % poloxamer 407.

In some embodiments, provided herein is a pharmaceutical formulation comprising:
(a) about 3 wt % of Compound I, or a pharmaceutically acceptable salt, solvate, or hydrate thereof;
(b) about 20 wt % of citric acid;
(c) about 10 wt % poloxamer 407;
(d) about 60 wt % mannitol;
(e) about 2 wt % stearic acid; and
(f) about 5 wt % crospovidone.

In some embodiments, provided herein is a pharmaceutical formulation comprising:
(a) Compound I maleate, or a solvate or hydrate thereof;
(b) citric acid; and
(c) a poloxamer.

In some embodiments, provided herein is a pharmaceutical formulation comprising:
(a) about 2 wt % to about 15 wt % of Compound I maleate, or a solvate or hydrate thereof;
(b) about 5 wt % to about 30 wt % of citric acid; and
(c) about 5 wt % to about 15 wt % a poloxamer.

In some embodiments, provided herein is a pharmaceutical formulation comprising:
(a) Compound I maleate, or a solvate or hydrate thereof;
(b) citric acid acid;
(c) a poloxamer (e.g., poloxamer 407); and
(d) a diluent (e.g., mannitol).

In some embodiments, provided herein is a pharmaceutical formulation comprising:
(a) about 2 wt % to about 15 wt % of Compound I maleate, or a solvate or hydrate thereof;
(b) about 5 wt % to about 30 wt % of citric acid;
(c) about 5 wt % to about 15 wt % poloxamer (e.g., poloxamer 407); and
(d) about 50 wt % to about 80 wt % diluent (e.g., mannitol).

In some embodiments, provided herein is a pharmaceutical formulation comprising:
(a) Compound I maleate, or a solvate or hydrate thereof;
(b) citric acid acid;
(c) a poloxamer (e.g., poloxamer 407);
(d) a diluent (e.g., mannitol); and
(e) a lubricant (e.g., stearic acid).

In some embodiments, provided herein is a pharmaceutical formulation comprising:
(a) about 2 wt % to about 15 wt % of Compound I maleate, or a solvate or hydrate thereof;
(b) about 5 wt % to about 30 wt % of citric acid;
(c) about 5 wt % to about 15 wt % poloxamer (e.g., poloxamer 407);
(d) about 50 wt % to about 80 wt % diluent (e.g., mannitol); and
(e) about 1 wt % to about 5 wt % lubricant (e.g., stearic acid).

In some embodiments, provided herein is a pharmaceutical formulation comprising:
(a) Compound I maleate, or a solvate or hydrate thereof;
(b) citric acid acid;
(c) a poloxamer (e.g., poloxamer 407);
(d) a diluent (e.g., mannitol);
(e) a lubricant (e.g., stearic acid); and
(f) a disintegrant (e.g., crospovidone).

In some embodiments, provided herein is a pharmaceutical formulation comprising:
(a) Compound I maleate, or a solvate or hydrate thereof;
(b) citric acid acid;
(c) a poloxamer (e.g., poloxamer 407);
(d) a diluent (e.g., mannitol);
(e) a lubricant (e.g., stearic acid);
(f) a disintegrant (e.g., crospovidone); and
(g) a glidant (e.g., colloidal silica).

In some embodiments, provided herein is a pharmaceutical formulation comprising:
(a) about 2 wt % to about 15 wt % of Compound I maleate, or a solvate or hydrate thereof;
(b) about 5 wt % to about 30 wt % of citric acid;

(c) about 5 wt % to about 15 wt % poloxamer (e.g., poloxamer 407);
(d) about 50 wt % to about 80 wt % diluent (e.g., mannitol);
(e) about 1 wt % to about 5 wt % lubricant (e.g., stearic acid); and
(f) about 2 wt % to about 5 wt % disintegrant (e.g., crospovidone).

In some embodiments, provided herein is a pharmaceutical formulation comprising:
(a) about 2 wt % to about 15 wt % of Compound I maleate, or a solvate or hydrate thereof;
(b) about 5 wt % to about 30 wt % of citric acid;
(c) about 5 wt % to about 15 wt % poloxamer 407;
(d) about 50 wt % to about 80 wt % mannitol;
(e) about 1 wt % to about 5 wt % stearic acid; and
(f) about 2 wt % to about 5 wt % crospovidone.

In some embodiments, provided herein is a pharmaceutical formulation comprising:
(a) about 12 wt % of Compound I maleate, or a solvate or hydrate thereof;
(b) about 20 wt % of citric acid; and
(c) about 10 wt % poloxamer 407.

In some embodiments, provided herein is a pharmaceutical formulation comprising:
(a) about 12 wt % of Compound I maleate, or a solvate or hydrate thereof;
(b) about 20 wt % of citric acid;
(c) about 10 wt % poloxamer 407;
(d) about 50 wt % mannitol;
(e) about 2 wt % stearic acid; and
(f) about 5 wt % crospovidone.

In some embodiments, provided herein is a pharmaceutical formulation comprising:
(a) about 3 wt % of Compound I maleate, or a solvate or hydrate thereof;
(b) about 20 wt % of citric acid; and
(c) about 10 wt % poloxamer 407.

In some embodiments, provided herein is a pharmaceutical formulation comprising:
(a) about 4 wt % of Compound I maleate, or a solvate or hydrate thereof;
(b) about 10 wt % of citric acid; and
(c) about 5 wt % poloxamer 407.

In some embodiments, provided herein is a pharmaceutical formulation comprising:
(a) about 7 wt % of Compound I maleate, or a solvate or hydrate thereof;
(b) about 10 wt % of citric acid; and
(c) about 5 wt % poloxamer 407.

In some embodiments, provided herein is a pharmaceutical formulation comprising:
(a) about 3 wt % of Compound I maleate, or a solvate or hydrate thereof;
(b) about 20 wt % of citric acid;
(c) about 10 wt % poloxamer 407;
(d) about 60 wt % mannitol;
(e) about 2 wt % stearic acid; and
(f) about 5 wt % crospovidone.

In some embodiments, provided herein is a pharmaceutical formulation comprising:
(a) about 4 wt % of Compound I maleate, or a solvate or hydrate thereof;
(b) about 10 wt % of citric acid;
(c) about 5 wt % poloxamer 407;
(d) about 76 wt % mannitol;
(e) about 2 wt % stearic acid;
(f) about 2.5 wt % crospovidone; and
(g) about 0.5 wt % colloidal silica.

In some embodiments, provided herein is a pharmaceutical formulation comprising:
(a) about 7 wt % of Compound I maleate, or a solvate or hydrate thereof;
(b) about 10 wt % of citric acid;
(c) about 5 wt % poloxamer 407;
(d) about 73 wt % mannitol;
(e) about 2 wt % stearic acid;
(f) about 2.5 wt % crospovidone; and
(g) about 0.5 wt % colloidal silica.

The pharmaceutical formulations in solid dosage forms provided herein which are suitable for oral administration can be prepared by blending Compound I maleate with an organic acid, and a surfactant. The pharmaceutical formulation formed can be further prepared to form a capsule.

In some embodiments, Compound I, or a pharmaceutically acceptable salt (e.g., Compound I maleate), solvate, or hydrate thereof, is in crystalline form. Crystalline form of Compound I maleate is disclosed in U.S. Provisional Application 62/564,070, the entireties of which is incorporated by reference. See also e.g., examples provided herein.

In some embodiments, the maleic acid salt of Compound I has at least one XRPD peak, in terms of 2-theta, selected from about 4.3°, about 8.4°, about 12.6°, about 13.2°, and about 18.5°. In some embodiments, the maleic acid salt of Compound I has at least two XRPD peaks, in terms of 2-theta, selected from about 4.3°, about 8.4°, about 12.6°, about 13.2°, and about 18.5°. In some embodiments, the maleic acid salt of Compound I has at least three XRPD peaks, in terms of 2-theta, selected from about 4.3°, about 8.4°, about 12.6°, about 13.2°, and about 18.5°. In some embodiments, the maleic acid salt of Compound I has at least four XRPD peak, in terms of 2-theta, selected from about 4.3°, about 8.4°, about 12.6°, about 13.2°, and about 18.5°. In some embodiments, the maleic acid salt of Compound I comprises the following XRPD peaks, in terms of 2-theta: about 4.3°, about 8.4°, about 12.6°, about 13.2°, and about 18.5°. In some embodiments, the maleic acid salt of Compound I comprises the following XRPD peaks, in terms of 2-theta: about 4.3°, about 8.4°, and about 13.2°.

In some embodiments, the maleic acid salt of Compound I has an XRPD profile substantially as shown in FIG. 1.

Figure 2:
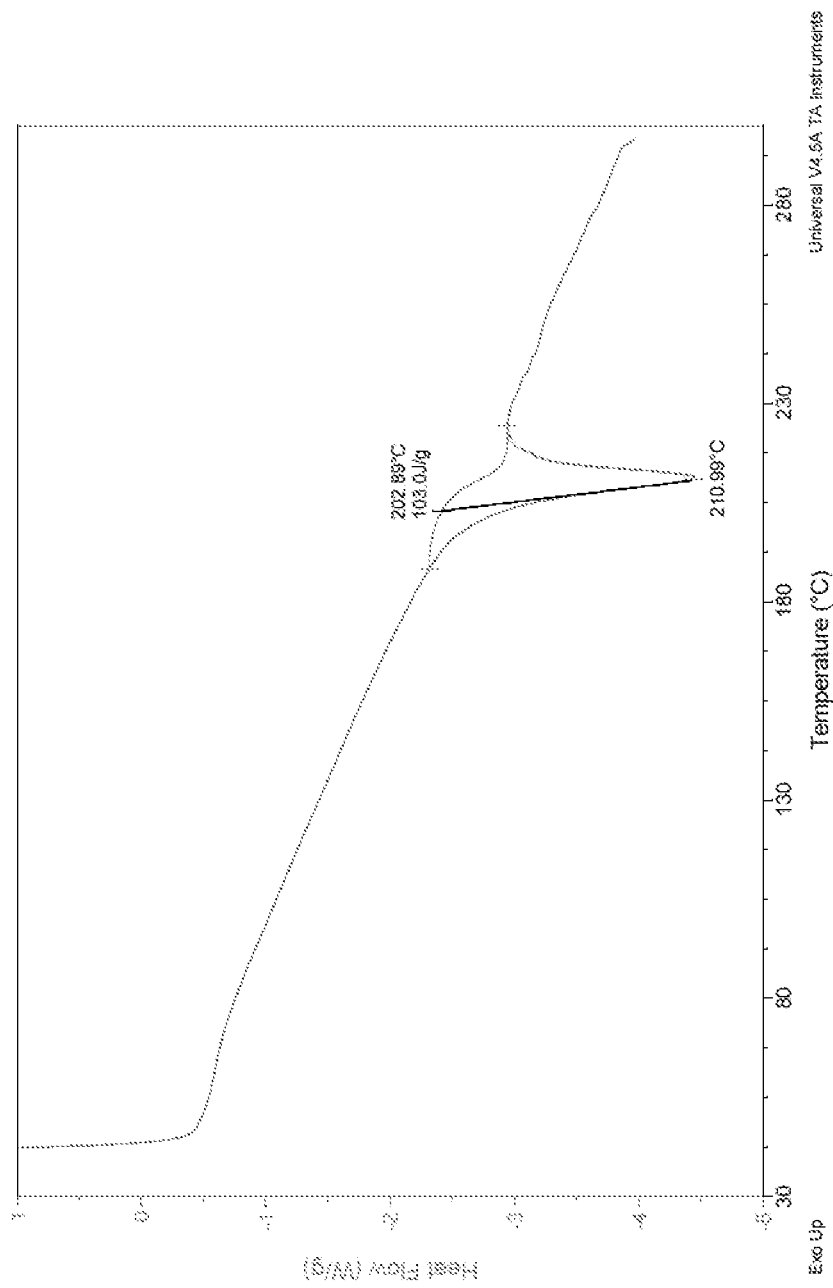
FIG. 2 shows a DSC thermogram representative of Compound I maleic acid salt.
Figure 3:
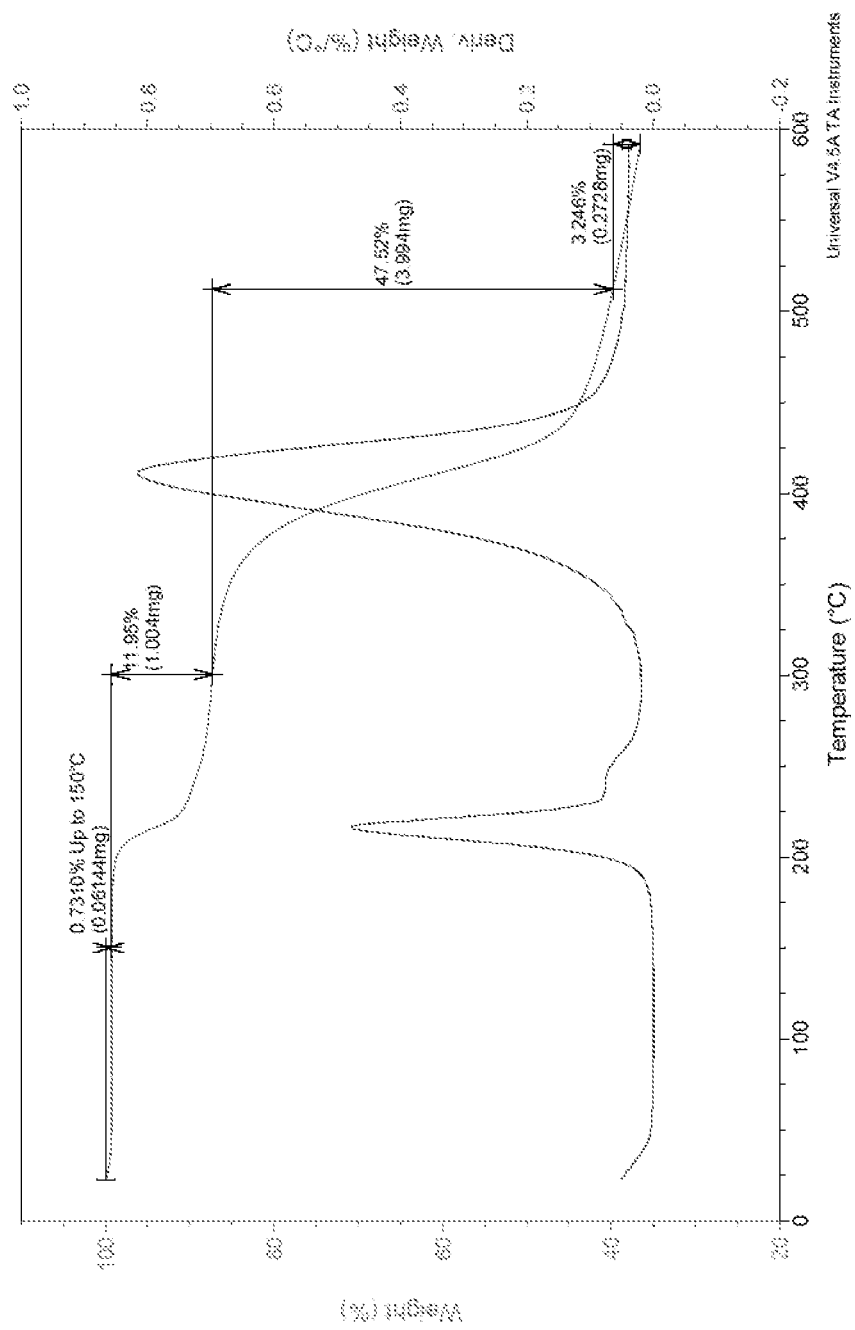
FIG. 3 shows TGA data representative of Compound I maleic acid salt.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation. In some embodiments, the maleic acid salt of Compound I has a DSC thermogram having an endothermic peak at about 211° C. In some embodiments, the maleic acid salt of Compound I has a DSC thermogram substantially as shown in FIG. 2. In some embodiments, the maleic acid salt of Compound I has a TGA thermogram substantially as shown in FIG. 3.

In some embodiments, Compound I, or a pharmaceutically acceptable salt (e.g., Compound I maleate), solvate, or hydrate thereof, is substantially isolated. By "substantially isolated" is meant that the salt or compound is at least partially or substantially separated from the environment in which it was formed or detected. Partial separation can include, for example, a composition enriched in the salts described herein. Substantial separation can include compositions containing at least about 50%, at least about 60%, at least about 70%, at least about 80%, at least about 90%, at least about 95%, at least about 97%, or at least about 99% by weight of the salts described herein, or salt thereof. Methods for isolating compounds and their salts are routine in the art.

The present application also relates to a solid dosage form comprising a pharmaceutical formulation provided herein. In some embodiments, the solid dosage form is suitable for oral administration. In some embodiment, the dosage form provided herein is in the form of tablets, capsules, pills, powders, sachets, and soft and hard gelatin capsules. In other embodiments, the dosage form provided herein is in the form of a capsule.

In preparing a formulation, Compound I, or a pharmaceutically acceptable salt (e.g., Compound I maleate), solvate, or hydrate thereof, can be milled to provide the appropriate particle size prior to combining with the other ingredients. Compound I maleate can be milled to a particle size of less than 200 mesh. The particle size can be adjusted by milling to provide a substantially uniform distribution in the formulation, e.g., about 40 mesh.

Compound I, or a pharmaceutically acceptable salt (e.g., Compound I maleate), solvate, or hydrate thereof, may be milled using known milling procedures to obtain a particle size appropriate for tablet formation and for other formulation types. Finely divided (nanoparticulate) preparations of the compounds of the invention can be prepared by processes known in the art, e.g., see International App. No. WO 2002/000196.

The formulations of the invention can include additional excipients. Examples of suitable additional excipients include dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. Other excipients include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The present invention further provides a dosage form which comprises any of the above-described formulations of the invention. The term "dosage form" refers to a physically discrete unit suitable as unitary dosages for human subjects and other mammals, each unit containing a predetermined quantity of active material calculated to produce the desired therapeutic effect, in association with a suitable pharmaceutical excipient.

For preparing solid dosage forms such as capsules, Compound I maleate can be mixed with excipients to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms (e.g., capsules) of the type described above containing from, for example, about 0.1 to about 1000 mg of Compound I, or a pharmaceutically acceptable salt (e.g., Compound I maleate), solvate, or hydrate thereof, on a free base basis. In some embodiments, the unit dosage forms (e.g., capsules) comprise about 1 to about 500 mg, about 1 to about 200, about 1 to about 100, about 1 to about 50, or about 1 to about 30 mg of Compound I, or a pharmaceutically acceptable salt (e.g., Compound I maleate), solvate, or hydrate thereof, on a free base basis. In some embodiments, the unit dosage forms (e.g., capsules) comprise about 5 to about 50 mg of Compound I, or a pharmaceutically acceptable salt (e.g., Compound I maleate), solvate, or hydrate thereof, on a free base basis, e.g., about 5 mg, about 10 mg, about 15 mg, about 20 mg, about 25 mg, about 30 mg, about 35 mg, about 40 mg, about 45 mg, or about 50 mg of Compound I, or a pharmaceutically acceptable salt (e.g., Compound I maleate), solvate, or hydrate thereof, on a free base basis. In some embodiments, unit dosage forms (e.g., capsules) comprise about 5 mg of Compound I, or a pharmaceutically acceptable salt (e.g., Compound I maleate), solvate, or hydrate thereof, on a free base basis. In some embodiments, unit dosage forms (e.g., capsules) comprise about 15 mg of Compound I, or a pharmaceutically acceptable salt (e.g., Compound I maleate), solvate, or hydrate thereof, on a free base basis. In some embodiments, unit dosage forms (e.g., capsules) comprise about 20 mg of Compound I, or a pharmaceutically acceptable salt (e.g., Compound I maleate), solvate, or hydrate thereof, on a free base basis. In some embodiments, unit dosage forms (e.g., capsules) comprise about 25 mg of Compound I, or a pharmaceutically acceptable salt (e.g., Compound I maleate), solvate, or hydrate thereof, on a free base basis.

Compound I, or a pharmaceutically acceptable salt (e.g., Compound I maleate), solvate, or hydrate thereof, unit dosage form (e.g., capsule) can be administered to a subject once daily, twice daily, three times daily, four times daily, etc. A person skilled in the art would know that two capsules of 5 mg can be administered together to obtain a 10 mg unit dosage. Compound I maleate may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, about 5 mg to about 200 mg of Compound I, or a pharmaceutically acceptable salt (e.g., Compound I maleate), solvate, or hydrate thereof, is administered to a subject once daily. In some embodiments, about 10 mg to about 100 mg of Compound I, or a pharmaceutically acceptable salt (e.g., Compound I maleate), solvate, or hydrate thereof, is administered to a subject once daily.

In some embodiments, about 5 mg to about 200 mg of Compound I maleate is administered to a subject once daily. In some embodiments, about 10 mg to about 100 mg of Compound I maleate is administered to a subject once daily. In some embodiments, about 10 mg of Compound I maleate is administered to a subject once daily (e.g., two capsules of 5 mg or one capsule of 10 mg per 24 hour period). In some embodiments, about 15 mg of Compound I maleate is administered to a subject once daily. In some embodiments, about 20 mg of Compound I maleate is administered to a subject once daily. In some embodiments, about 25 mg of Compound I maleate is administered to a subject once daily. In some embodiments, about 40 mg of Compound I maleate is administered to a subject once daily. In some embodiments, about 50 mg of Compound I maleate is administered to a subject once daily. In some embodiments, about 75 mg of Compound I maleate is administered to a subject once daily. In some embodiments, about 80 mg of Compound I maleate is administered to a subject once daily. In some embodiments, about 100 mg of Compound I maleate is administered to a subject once daily. In some embodiments, about 150 mg of Compound I maleate is administered to a subject once daily. In some embodiments, about 160 mg of Compound I maleate is administered to a subject once daily. In some embodiments, about 200 mg of Compound I maleate is administered to a subject once daily.

Definitions

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include dihydroxyfuranone.

As used herein, maleic acid is also known as cis-butenedioic acid.

As used herein, and unless otherwise specified, the term "about," when used in connection with a numeric value or range of values which is provided to describe a particular salt or solid form, e.g., a specific temperature or temperature range, such as, for example, that describing a melting, dehydration, or glass transition; a mass change, such as, for example, a mass change as a function of temperature or humidity; a solvent or water content, in terms of, for example, mass or a percentage; or a peak position, such as, for example, in analysis by, for example, $^{13}$C NMR, DSC, TGA and XRPD; indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, or 1% of the recited value or range of values while still describing the particular solid form. In some embodiments, the term "about" indicates that the numeric value or range of values may vary by 5%. The term "about", when used in reference to a degree 2-theta value refers to +/−0.3 degrees 2-theta or +/−0.2 degrees 2-theta. As used herein, the terms "blend," "blending," and "blended" refer to combining or mixing different substance to obtain a mixture. The resulting blended mixture can be homogeneous.

The term "hydrate," as used herein, is meant to refer to a solid form of Compound I maleic acid salt that includes water. The water in a hydrate can be present in a stoichiometric amount with respect to the amount of salt in the solid, or can be present in varying amounts, such as can be found in connection with channel hydrates. In some embodiments, Compound I maleic acid salt is a mono-hydrate (e.g., the molar ratio of the salt to water is about 1:1). In some embodiments, Compound I maleic acid salt is a di-hydrate (e.g., the molar ratio of the salt to water is about 1:2). In some embodiments, Compound I maleic acid salt is a hemi-hydrate (e.g., the molar ratio of the salt to water is about 2:1). In some embodiments, Compound I maleic acid salt has one or more molecules of water per molecule of salt.

Compound I, or a pharmaceutically acceptable salt (e.g., Compound I maleate), can also be in a solvated form. The term "solvate" means a solid form that includes solvent molecules with Compound I or its pharmaceutically acceptable salts (e.g. maleic acid salt). The solvent can be an organic compound, an inorganic compound, or a mixture of both. A solvate where the solvent is water is generally referred to as a "hydrate" or "hydrated form." The term "hydrate" means a solid form that includes water molecules with Compound I or its pharmaceutically acceptable salts (e.g. maleic acid salt).

As used herein, the term "anhydrous" refers to a compound (e.g., Compound I, Compound I maleate) that does not include water or solvents. For example, Compound I or its maleate salt can be in a solid form that is free of water or solvent, e.g., less than 1%, 0.5%, 0.4%, 0.3%, 0.2%, or 0.1% by weight of water or solvent is present.

As used herein, the term "peak" or "characteristic peak" refers to a reflection having a relative height/intensity of at least about 3% of the maximum peak height/intensity. As used herein, the term "crystalline" or "crystalline form" refers to a crystalline solid form of a chemical compound, including, but not limited to, a single-component or multiple-component crystal form, e.g., including solvates, hydrates, clathrates, and co-crystals.

The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the crystalline form as well as help determine stability and solvent/water content.

Different crystalline forms of a particular substance, such as Compound I, or a pharmaceutically acceptable salt (e.g., Compound I maleate), solvate, or hydrate thereof, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters used, the sample mounting procedure, and the particular instrument employed. In some instances, new peaks may be observed or existing peaks may disappear, depending on the type of the machine or the settings (for example, whether a Ni filter is used or not). As used herein, the term "peak" refers to a reflection having a relative height/intensity of at least about 3% or at least about 4% of the maximum peak height/intensity. Moreover, instrument variation and other factors can affect the 2-theta values. Thus, peak assignments, such as those reported herein, can vary by plus or minus about 0.2° (2-theta) or about 0.3° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, exposure to moisture, grinding and solvent-drop grinding.

As used herein, the term "amorphous" or "amorphous form" is intended to mean that the substance, component, or product in question is not substantially crystalline as determined, for instance, by XRPD or where the substance, component, or product in question, for example is not birefringent when viewed microscopically. In certain embodiments, a sample comprising an amorphous form of a substance may be substantially free of other amorphous forms and/or crystalline forms. For example, an amorphous substance can be identified by an XRPD spectrum having an absence of reflections.

In some embodiments, Compound I, or a pharmaceutically acceptable salt (e.g., Compound I maleate), solvate, or hydrate thereof, provided herein are prepared in batches referred to as batches, samples, or preparations. The batches, samples, or preparations can include Compound I, or a pharmaceutically acceptable salt (e.g., Compound I maleate), solvate, or hydrate thereof, in any of the crystalline or non-crystalline forms described herein, included hydrated and non-hydrated forms, and mixtures thereof.

As used herein, the term "crystalline purity," means percentage of a crystalline form in a preparation or sample which may contain other forms such as an amorphous form of the same compound, or at least one other crystalline form of the compound, or mixtures thereof.

As used herein, the term "substantially crystalline," means a majority of the weight of a sample or preparation of Compound I, or a pharmaceutically acceptable salt (e.g., Compound I maleate), solvate, or hydrate thereof, is crystalline and the remainder of the sample is a non-crystalline form (e.g., amorphous form) of Compound I, or a pharmaceutically acceptable salt (e.g., Compound I maleate), solvate, or hydrate thereof. In some embodiments, a substantially crystalline sample has at least about 95% crystallinity (e.g., about 5% of the non-crystalline form), preferably at least about 96% crystallinity (e.g., about 4% of the non-crystalline form), more preferably at least about 97% crystallinity (e.g., about 3% of the non-crystalline form), even more preferably at least about 98% crystallinity (e.g., about 2% of the non-crystalline form), still more preferably at least about 99% crystallinity (e.g., about 1% of the non-crystalline form), and most preferably about 100% crystallinity (e.g., about 0% of the non-crystalline form). In some embodiments, the term "fully crystalline" means at least about 99% or about 100% crystallinity.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

Various pharmaceutically acceptable excipients can be used in the formulations described herein. As used herein, "pharmaceutically acceptable excipient" refers to a pharmaceutically-acceptable material, composition, or vehicle, such as a liquid or solid filler, diluent, solvent, or encapsulating material. Excipients are generally safe, non-toxic and neither biologically nor otherwise undesirable and include excipients that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "contacting" refers to the bringing together of indicated moieties in an in vitro system or an in vivo system. For example, "contacting" an AXL/MER kinase with a compound of the invention includes the administration of a compound of the present invention to an individual or patient, such as a human, having an AXL/MER kinase, as well as, for example, introducing a compound of the invention into a sample containing a cellular or purified preparation containing the ALX/MER kinase.

As used herein, the term "individual," "patient," or "subject" used interchangeably, refers to any animal, including mammals, preferably mice, rats, monkeys, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Methods of Use

Compound I, or a pharmaceutically acceptable salt (e.g., Compound I maleate), solvate, or hydrate thereof, of the present disclosure can modulate or inhibit the activity of AXL/MER kinases. For example, Compound I, or a pharmaceutically acceptable salt (e.g., Compound I maleate), solvate, or hydrate thereof, can be used to inhibit activity of ALX/MER kinases in a cell or in an individual or patient in need of inhibition of the kinases by administering an inhibiting amount of Compound I maleate to the cell, individual, or patient. Therefore, pharmaceutical formulations comprising Compound I maleate can be used to inhibit activity of AXL/MER kinases.

In some embodiments, Compound I, or a pharmaceutically acceptable salt (e.g., Compound I maleate), solvate, or hydrate thereof, is selective for the AXL/MER kinases over one or more of other kinases. In some embodiments, the selectivity is 2-fold or more, 3-fold or more, 5-fold or more, 10-fold or more, 25-fold or more, 50-fold or more, or 100-fold or more.

Compound I, or a pharmaceutically acceptable salt (e.g., Compound I maleate), solvate, or hydrate thereof, can inhibit one or more of AXL and MER. In some embodiments, Compound I, or a pharmaceutically acceptable salt (e.g., Compound I maleate), solvate, or hydrate thereof, is selective for one TAM kinase over another. "Selective" means that the compound binds to or inhibits a TAM kinase with greater affinity or potency, respectively, compared to a reference enzyme, such as another TAM kinase. For example, Compound I, or a pharmaceutically acceptable salt (e.g., Compound I maleate), solvate, or hydrate thereof, can be selective for AXL over MER and TYRO3, selective for MER over AXL and TYRO3, or selective for AXL and MER over TYRO3. In some embodiments, Compound I, or a pharmaceutically acceptable salt (e.g., Compound I maleate), solvate, or hydrate thereof, is selective for AXL and MER over TYRO3 and other kinases. In some embodiments, provided herein is a method for inhibiting AXL and MER kinase, which comprises contacting the AXL and MER kinase with Compound I, or a pharmaceutically acceptable salt (e.g., Compound I maleate), solvate, or hydrate thereof.

As an ALX/MER kinases inhibitor, Compound I, or a pharmaceutically acceptable salt (e.g., Compound I maleate), solvate, or hydrate thereof, is useful in the treatment of various diseases associated with abnormal expression or activity of the AXL/MER kinases. Compound I, or a pharmaceutically acceptable salt (e.g., Compound I maleate), solvate, or hydrate thereof, will be useful in providing a means of preventing the growth or inducing apoptosis in tumors, particularly by inhibiting angiogenesis. It is therefore anticipated that Compound I, or a pharmaceutically acceptable salt (e.g., Compound I maleate), solvate, or hydrate thereof, will prove useful in treating or preventing proliferative disorders such as cancers. In particular, tumours with activating mutants of receptor tyrosine kinases or upregulation of receptor tyrosine kinases may be particularly sensitive to the inhibitors.

In certain embodiments, the disclosure provides a method for treating a disease or disorder mediated by ALX/MER kinases in a patient in need thereof, comprising the step of administering to said patient pharmaceutical formulation comprising Compound I, or a pharmaceutically acceptable salt (e.g., Compound I maleate), solvate, or hydrate thereof.

For example, the pharmaceutical formulation of the disclosure are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Other cancers treatable with the compounds of the disclosure include bone cancer, intraocular cancers, gynecological cancers, cancer of the endocrine system, cancer of the adrenal gland, sarcoma of soft tissue, cancer of the urethra, cancer of the penis, pituitary cancer, triple-negative breast cancer (TNBC) and environmentally induced cancers including those induced by asbestos.

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the pharmaceutical formulation of the disclosure include tumors of the eye, glioblastoma, melanoma, rhabdosarcoma, lymphosarcoma, and osteosarcoma.

Pharmaceutical formulations of the disclosure can also be useful in the inhibition of tumor metastasis.

In some embodiments, diseases and indications that are treatable using pharmaceutical formulation of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), small lymphocytic lymphoma (SLL), chronic myelogenous leukemia (CML), diffuse large B-cell lymphoma (DLBCL), mantle cell lymphoma (MCL), marginal zone lymphoma (MZL), Non-Hodgkin lymphoma (including relapsed or refractory NHL), follicular lymphoma (FL), Hodgkin lymphoma, lymphoblastic lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, peripheral T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer and bile duct cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma, urothelial carcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma, Lhermitte-Duclos disease, neoplasm of the central nervous system (CNS), primary CNS lymphoma and spinal axis tumor.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, the present disclosure provides a method for treating hepatocellular carcinoma in a patient in need thereof, comprising the step of administering to said patient a pharmaceutical formulation described herein.

In some embodiments, the present disclosure provides a method for treating Rhabdomyosarcoma, esophageal cancer, breast cancer, or cancer of a head or neck, in a patient in need thereof, comprising the step of administering to said patient a pharmaceutical formulation described herein.

In some embodiments, the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

In some embodiments, the cancer is selected from cancer is selected from hepatocellular cancer, bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

In some embodiments, the cancer is selected from the cancer is lung cancer, prostate cancer, colon cancer, breast cancer, melanoma, renal cell carcinoma, multiple myeloma, gastric cancer, and rhabdomyosarcoma.

Targeting TAM receptor tyrosine kinases can provide a therapeutic approach to treat viral diseases (T Shibata, et al. *The Journal of Immunology*, 2014, 192, 3569-3581). The present disclosure provides a method for treating infections such as viral infections. The method includes administering to a patient in need thereof, a therapeutically effective amount of a pharmaceutical formulation described herein.

Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, Marburg virus and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses (for example: West Nile, dengue, tick-borne encephalitis, yellow fever, Zika), echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In some embodiments, the present disclosure provides a method for treating thrombus formation (J.M.E.M. Cosemans et al. *J. of Thrombosis and Haemostasis* 2010, 8, 1797-1808 and A. Angelillo-Scherrer et al. *J. Clin. Invest.* 2008, 118, 583-596).

In some embodiments, the salts of the present disclosure may be useful in preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

General Methods

Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification," K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization," K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization," K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A:

0.15% NH₄OH in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization," K. Blom, B. Glass, R. Sparks, A. Combs, *J. Comb. Chem.*, 6, 874-883 (2004)]. Typically, the flow rate used with 30×100 mm column was 60 mL/minute.

Example 1. Preparation of Capsules

Capsules of Compound I maleate are prepared as follows. Compound I maleate used in the formulations described below are crystalline and are prepared according to Examples 4-6.
Procedures for 20 mg (as Free Base)

TABLE 1A 20 mg Capsules Formulation B

| Component | % | mg/capsule | Batch (mg) |
|---|---|---|---|
| Compound I Maleate | 11.80 | 23.60 | 354.00 |
| Mannitol | 51.20 | 102.40 | 1536.00 |
| Citric Acid Monohydrate NF | 20.00 | 40.00 | 600.00 |
| Poloxamer 407 | 10.00 | 20.0 | 300.00 |
| Crospovidone | 5.00 | 10.00 | 150.00 |
| Stearic Acid | 2.00 | 4.00 | 60.00 |
| Total | 100.00 | 200.0 | 3000.00 |

Mannitol (diluent), citric acid (pH modifier), crospovidone (disintegrant), poloxamer 407 (surfactant) and stearic acid (lubricant) were passed through 40 mesh sieve and weighed. The excipients were added to a 20 cc glass vial. The milled drug substance was weighed and added to the vial. The components were mixed by hand with a spatula within the vial. The entire contents were then passed through a 30 mesh screen (3 times) to homogenize the blend. The final blend was filled into size 2 capsules (Vcaps® Plus (HPMC (hydroxypropylmethylcellulose) capsules) from Capsugel). The ratio of Compound I as base to citric acid to poloxamer 407:1 to 2 to 1.

Other 20 mg capsules (Formulations A, C, D, and E) were prepared in a similar manner.

TABLE 1B 20 mg Capsules Formulation A

| Component | % | mg/capsule | Batch (mg) |
|---|---|---|---|
| Compound I Maleate | 11.80 | 23.60 | 708.00 |
| Mannitol USP | 61.20 | 122.40 | 3672.00 |
| Citric Acid Monohydrate USP | 20.00 | 40.00 | 1200.00 |
| Crospovidone NF | 5.00 | 10.00 | 300.00 |
| Stearic Acid NF | 2.00 | 4.00 | 120.00 |
| Total | 100.00 | 200.0 | 6000.00 |

TABLE 1C 20 mg Capsules Formulation C

| Component | % | mg/capsule | Batch (mg) |
|---|---|---|---|
| Compound I Maleate | 11.80 | 23.60 | 354.00 |
| Mannitol USP | 56.20 | 112.40 | 1686.00 |
| Citric Acid Monohydrate USP | 20.00 | 40.00 | 600.00 |
| Sodium Lauryl Sulfate NF | 5.00 | 10.0 | 150.00 |
| Crospovidone NF | 5.00 | 10.00 | 150.00 |
| Stearic Acid NF | 2.00 | 4.00 | 60.00 |
| Total | 100.00 | 200.0 | 3000.00 |

TABLE 1D 20 mg Capsules Formulation D

| Component | % | mg/capsule | Batch (mg) |
|---|---|---|---|
| Compound I Maleate | 11.80 | 23.60 | 354.00 |
| Mannitol USP | 71.20 | 142.40 | 2136.00 |
| Poloxamer 407 USP-NF | 10.00 | 20.0 | 300.00 |
| Crospovidone NF | 5.00 | 10.00 | 150.00 |
| Stearic Acid NF | 2.00 | 4.00 | 60.00 |
| Total | 100.00 | 200.0 | 3000.00 |

TABLE 1E 20 mg Capsules Formulation E

| Component | % | mg/capsule | Batch (mg) |
|---|---|---|---|
| Compound I Maleate | 11.80 | 23.60 | 354.00 |
| Mannitol USP | 51.20 | 102.40 | 1536.00 |
| Citric Acid Monohydrate USP | 20.00 | 40.00 | 600.00 |
| Poloxamer 188 USP-NF | 10.00 | 20.0 | 300.00 |
| Crospovidone NF | 5.00 | 10.00 | 150.00 |
| Stearic Acid NF | 2.00 | 4.00 | 60.00 |
| Total | 100.00 | 200.0 | 3000.00 |

Procedures for 25 mg (as Free Base)

TABLE 1F 25 mg Capsules

| Component | % | mg/capsule | Batch (g) |
|---|---|---|---|
| Compound I Maleate | 7.38 | 29.50 | 8.85 |
| Mannitol USP | 72.63 | 290.50 | 87.15 |
| Citric Acid Monohydrate USP | 10.00 | 40.00 | 12.00 |
| Poloxamer 407 Micro USP/NF | 5.00 | 20.0 | 6.00 |
| Crospovidone USP | 2.50 | 10.00 | 3.00 |
| Stearic Acid NF | 2.00 | 8.00 | 2.40 |
| Colloidal Silica USP/NF | 0.50 | 2.00 | 0.60 |
| Total | 100.00 | 400.0 | 120.00 |

Mannitol, citric acid monohydrate, poloxamer 407, crospovidone, and stearic acid were screened with a 40 mesh sieve and weighed. Mannitol, citric acid, and poloxmer 407 were added to a 500 ml glass jar and mixed on a turbula mixer for 5 minutes on speed 32. Milled drug substance was added and then mixed for 5 minutes. The entire blend was screened through a 40 mesh sieve twice and then returned to the jar. Crospovidone was added and mixed for 2 minutes. Colloidal silica was added to 5 g of blend, mixed by hand, screened with a 40 mesh sieve and returned to the jar along with the stearic acid. The blend was mixed for 3 additional minutes on the turbula mixer. The final blend was filled into size 0 capsules (Vcaps Plus-Capsugel). The ratio of Compound I as base to citric acid to poloxamer 407:1 to 1.6 to 0.8.

Alternative Procedure for 25 mg (as a Free Base)

TABLE 1G 25 mg Capsules

| Component | % | mg/capsule | Batch (g) |
|---|---|---|---|
| Compound I Maleate | 7.38 | 29.52 | 354.24 |
| Mannitol USP | 72.62 | 290.48 | 3485.76 |
| Citric Acid Monohydrate NF | 10.00 | 40.00 | 480.00 |
| Poloxamer 407 Micro USP/NF | 5.00 | 20.00 | 240.00 |
| Crospovidone USP | 2.50 | 10.00 | 120.00 |
| Stearic Acid NF | 2.00 | 8.00 | 96.00 |
| Colloidal Silica USP/NF | 0.50 | 2.00 | 24.00 |
| Total | 100.00 | 400.0 | 4800.00 |

The components were weighed. The following materials were milled through a Quadro Comil (039 screen) at a speed of 1500±100 RPM: half of the required mannitol, poloxamer 407, milled Compound I maleate, and crospovidone. The milled blend was collected. Citric acid and colloidal silica were mixed in a bag, and then passed through Comil followed by the remainder of mannitol. Both blends were added to a 16Q blender and mixed for 18 minutes at 21 RPM. The resulting blend was passed through the Comil and blended for 18 additional minutes. The blend was then passed through the Comill. Screened (30 mesh) stearic acid was added and blended for 3.5 additional minutes. The final blend was discharged and encapsulated into size 0 capsules (V-caps plus) with a Bosch Encapsulator at a target fill weight of 400 mg. The ratio of Compound I as base to citric acid to poloxamer 407:1 to 1.6 to 0.8.

Procedures for 5 mg (as Free Base)

TABLE 1H 5 mg Capsules

| Component | % | mg/capsule | Batch (g) |
|---|---|---|---|
| Compound I Maleate | 2.95 | 5.90 | 118.0 |
| Mannitol USP | 59.55 | 119.10 | 2382.0 |
| Citric Acid Monohydrate NF | 20.00 | 40.00 | 800.0 |
| Poloxamer 407 Micro USP/NF | 10.00 | 20.0 | 400.0 |
| Crospovidone USP | 5.00 | 10.00 | 200.0 |
| Stearic Acid NF | 2.00 | 4.00 | 80.0 |
| Colloidal Silica USP/NF | 0.50 | 1.00 | 20.0 |
| Total | 100.00 | 200.0 | 4000.0 |

The components were weighed. The following materials were milled through a Quadro Comil (039 screen) at a speed of 1500±100 RPM: ½ of required mannitol, poloxamer 407, milled Compound I maleate, and crospovidone. The milled blend was collected. Citric acid and colloidal silica were mixed in a bag, and then passed through Comil followed by the remainder of mannitol. Both blends were added to a 16Q blender and mixed for 18 minutes at 21 RPM. The resulting blend was passed through the Comil and blended for 18 additional minutes. The blend was then passed through the Comill. Screened (30 mesh) stearic acid was added and blended for 3.5 additional minutes. The final blend was discharged and encapsulated into size 2 capsules (V-caps plus) with a Bosch Encapsulator at a target fill weight of 200 mg. The ratio of Compound I as base to citric acid to poloxamer 407:1 to 8 to 4.

Procedures for 15 mg (as Free Base)

TABLE 1I 15 mg Capsules

| Component | % | mg/capsule | Batch (g) |
|---|---|---|---|
| Compound I Maleate | 4.43 | 17.72 | 354.4 |
| Mannitol USP | 75.57 | 302.28 | 6045.6 |
| Citric Acid Monohydrate NF | 10.00 | 40.00 | 800.0 |
| Poloxamer 407 Micro USP/NF | 5.00 | 20.00 | 400.0 |
| Crospovidone USP | 2.50 | 10.00 | 200.0 |
| Stearic Acid NF | 2.00 | 8.00 | 160.0 |
| Colloidal Silica USP/NF | 0.50 | 2.00 | 40.0 |
| Total | 100.00 | 400.0 | 8000.0 |

The components were weighed. The following materials were milled through a Quadro Comil (039 screen) at a speed of 1500±100 RPM: ½ of required mannitol, poloxamer 407, milled Compound I maleate, and crospovidone. The milled blend was collected. Citric acid and colloidal silica were mixed in a bag, and then passed through Comil followed by the remainder of mannitol. Both blends were added to a 16Q blender and mixed for 18 minutes at 21 RPM. The resulting blend was passed through the Comil and blended for 18 additional minutes. The blend was then passed through the Comill. Screened (30 mesh) stearic acid was added and blended for 3.5 additional minutes. The final blend was discharged and encapsulated into size 0 capsules (V-caps plus) with a Bosch Encapsulator at a target fill weight of 400 mg. The ratio of Compound I as base to citric acid to poloxamer 407:1 to 2.67 to 1.33

Example 2. Bioavailability Studies

Capsules of Compound I maleate (20 mg as a free base) from Example 1 were used in the following bioavailability studies. Specifically, the procedures for preparing formulation B in Table 2A are detailed in Example 1. Other formulations in Table 2A were also prepared in a similar manner as the 20 mg capsules in Example 1.

The purpose of this study was to determine the impact of formulation components on the pharmacokinetic properties of Compound I maleate following administration of Compound maleate capsules. The in-life portion of this study was performed at New Iberia Research Center (NIRC) of University of Louisiana at Lafayette and adhered to the study protocol and NIRC standard operating procedures.

Four male cynomolgus monkey subjects were fasted for at least 12 hours and received an oral dose containing Compound I maleate administered by pill gun. Serial blood samples were collected pre-dose, 15, 30 min., and 1, 2, 3, 4, 6, 8, 12, 16, and 24 hours post dose. The blood was placed on wet ice and centrifuged under refrigeration to obtain plasma and stored frozen at approximately −20° C. Plasma samples were shipped to Incyte Corporation (Wilmington, DE) on dry ice for analysis.

Plasma and urine concentrations of Compound I were determined at Incyte Corporation under non-GLP conditions. The method combined a protein precipitation extraction and LC/MS/MS analysis. The plasma concentration-time data were used to determine the pharmacokinetic parameters for each animal by standard non-compartmental methods using IDBS E-Workbook Suite PK template (E-Workbook version 9.4.0 Build 18, IDBS, Inc., Alameda, CA).

TABLE 2A

Bioavailability results from 20 mg of Compound I capsules

| Formulation no | Mannitol | Citric acid | Crospov | Pol. 407 | Pol. 188 | SLS | Stearic acid | Cyno PK AUC | SD |
|---|---|---|---|---|---|---|---|---|---|
| A | X | X | X | | | | X | 3620 | 2980 |
| B | X | X | X | X | | | X | 9080 | 2630 |
| C | X | X | X | | | X | X | 1390 | 818 |
| D | X | | X | X | | | X | 2750 | 2560 |
| E | X | X | X | | X | | X | 5980 | 1330 |

A similar study was carried out using capsules of Compound I maleate (5 mg as a free base) from Example 1. The 5 mg formulations are prepared using Vcaps® Plus capsules (HPMC (hydroxypropylmethylcellulose) capsules) from Capsugel.

TABLE 2B

Comparison of Pharmacokinetic Parameters following Administration of 5.0 mg Capsules in Cynomolgus Monkeys

| Parameter | value |
|---|---|
| $C_{max}$ (nM) | 319 ± 175 |
| $T_{max}$ (h) | 3.25 ± 0.96 |
| $AUC_{inf}$ (nM * h) | 1790 ± 968 |
| $t^{1/2}$ (h) | 4.44 ± 1.3 |

Example 3. Solubility Study

The solubility of Compound I maleate was determined in aqueous solution in the presence of several surfactants at 37° C. The surfactants included sodium lauryl sulfate (SLS), poloxamer 188, and poloxamer 407 at a concentration of 0.2% (w/v) in water; a vessel without surfactant was included as a control. The experiment was performed in a Distek 2100 dissolution bath using 500 ml of media stirred at 100 RPM (USP type II dissolution apparatus). 100 mg of drug substance (free base equivalent) was added to the media to give a theoretical maximum concentration of 0.20 mg/ml. 5 ml samples were taken and filtered with a 0.45 micron GHP filter prior to analysis by HPLC. Listed below are the observed concentrations for the samples after 60 minutes of stirring time.

| Media | Concentration (mg/mL) |
|---|---|
| water | 0.007 |
| 0.2% SLS | >0.20 |
| 0.2% Poloxamer 188 | 0.018 |
| 0.2% Poloxamer 407 | 0.009 |

The data indicated that the solubility in sodium lauryl sulfate solution was significantly higher than water, or solutions of poloxamer. The drug substance completely dissolved in the presence of 0.2% SLS to form a clear solution.

Example 4. Synthesis of N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide Maleate (Compound I Maleate) Scheme 1

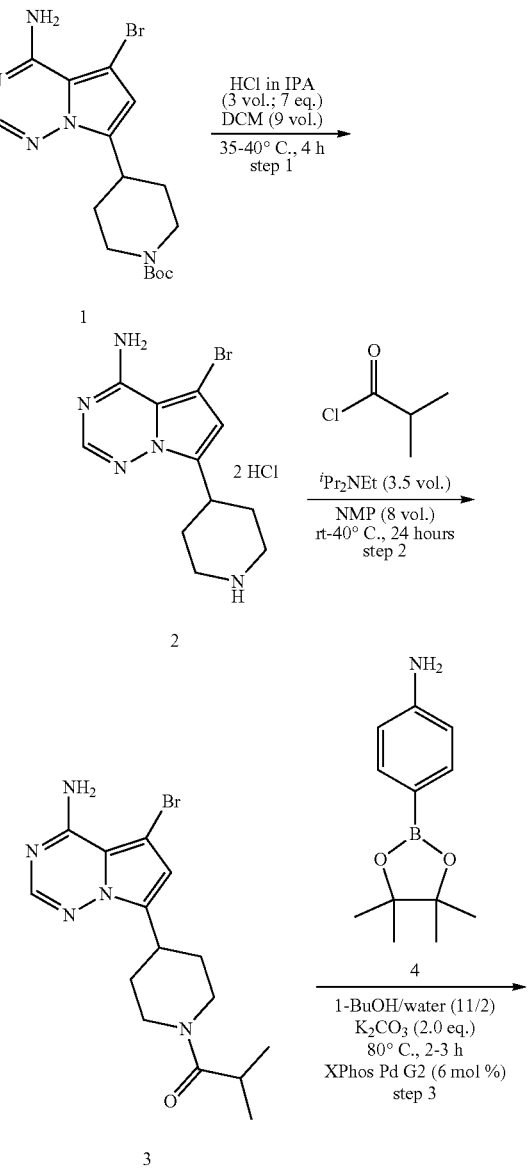

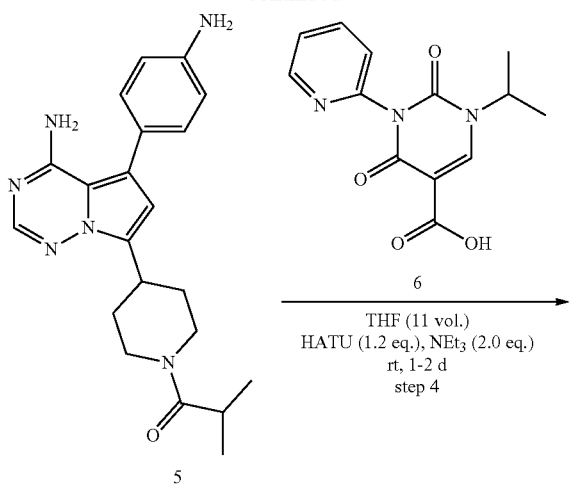

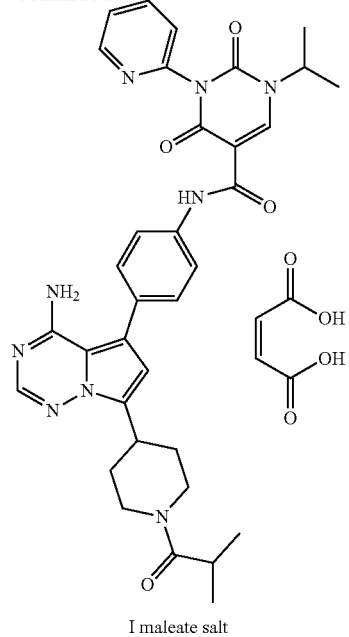

I maleate salt

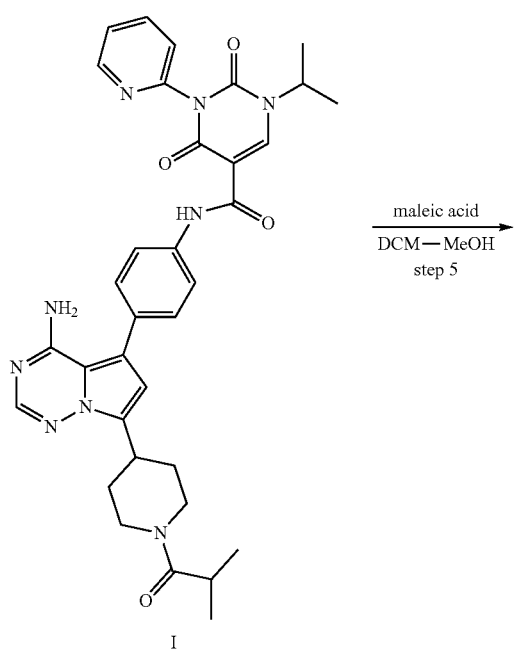

I

Step 1. 5-Bromo-7-(piperidin-4-yl)pyrrolo[1,2-f][1,2,4]triazin-4-amine dihydrochloride (Compound 2)

In a 5-necked 22-L round bottom flask equipped with a mechanical stirrer, a heating mantle, a thermal couple, a reflux conderser, a nitrogen inlet and a nitrogen outlet was placed tert-butyl 4-(4-amino-5-bromopyrrolo[2,1-f][1,2,4]triazin-7-yl)piperidine-1-carboxylate (Compound 1, 880 g, 2.221 mol) in dichloromethane (DCM, 8.0 L) at room temperature. To the suspension was added hydrochloric acid in 2-propanol (5.8 N, 2.7 L, 15.66 mol, 7.05 eq.). The mixture was heated to 35° C. After 4 hours, the reaction mixture was diluted with tert-butyl methyl ether (TBME, 4.5 L). The resulting mixture was cooled to room temperature, filtered and washed with TBME (2.0 L). The cake was dried on the filter under house vacuum for 24 hours to provide 5-bromo-7-(piperidin-4-yl)pyrrolo[1,2-f][1,2,4]triazin-4-amine dihydrochloride (Compound 2, 848 g, 103%) as a light brown solid. $^1$H NMR (400 MHZ, DMSO-$d_6$) δ 9.53-9.29; (m, 3H), 8.23; (s, 1H), 6.91; (s, 1H), 3.38; (tt, J=11.8, 3.6 Hz, 1H), 3.30; (d, J=12.4 Hz, 2H), 3.00; (dtd, J=12.8, 10.1, 2.6 Hz, 2H), 2.07; (dd, J=14.1, 3.8 Hz, 2H), 1.97-1.87; (m, 2H) ppm; $^{13}$C NMR (101 MHz, DMSO-$d_6$) δ 150.34, 139.32, 138.92, 113.24, 109.67, 95.70, 43.06, 30.57, 26.89 ppm; $C_{11}H_{14}BrN_5$ (MW 295.0), LCMS (EI) m/e 296.0 (M$^+$+H).

Step 2. 1-(4-(4-Amino-5-bromopyrrolo[1,2-f][1,2,4]triazin-7-yl)piperidin-1-yl)-2-methylpropan-1-one (Compound 3)

In a 5-necked 22-L round bottom flask equipped with a mechanical stirrer, a thermal couple, a reflux conderser, a nitrogen inlet and a nitrogen outlet was placed 5-bromo-7-(piperidin-4-yl)pyrrolo[1,2-f][1,2,4]triazin-4-amine dihydrochloride (Compound 2, 1300 g, 3.522 mol) in N-methyl piperidinone (NMP, 10 L) at room temperature. To the suspension was added N,N-diisopropylethylamine (1593 g, 12.3 mol). The mixture was cooled to 10° C. before charging isobutyryl chloride (388 g, 3.645 mol). The reaction was agitated at room temperature, and monitored by HPLC. Extra isobutyryl chloride (22.5 g, 0.211 mol) was added to consume all the starting material. Once the reaction was completed, the reaction mixture was filtered through a Celite pad. The resulting filtrate was cooled to 10° C., water (26 L) was added gradually to precipitate out the product. The solids were collected by filtration, and washed by water (12 L). The cake was dried on the filter under house vacuum for 48 hours to provide 1-(4-(4-amino-5-bromopyrrolo[1,2-f][1,2,4]triazin-7-yl)piperidin-1-yl)-2-methylpropan-1-one (Compound 3, 1095 g, 85%) as a light brown solid. $^1$H NMR (400 MHZ, DMSO-$d_6$) δ 7.86; (s, 1H), 6.64; (s, 1H), 4.51; (d, J=12.6 Hz, 1H), 4.01; (d, J=13.2 Hz, 1H), 3.35-3.30; (m, 1H), 3.12; (t, J=12.3 Hz, 1H), 2.91-2.84; (m, 1H), 2.64; (t, J=12.1 Hz, 1H), 2.02-1.93; (m, 2H), 1.55-1.42; (m, 2H), 1.02; (d, J=6.5 Hz, 3H), 1.00; (d, J=6.5 Hz, 3H) ppm; $^{13}$C NMR (101 MHZ, DMSO-$d_6$) δ 174.50, 155.68, 148.37, 135.22, 111.36, 110.65, 87.27, 45.34, 41.67, 32.91, 31.30, 30.33, 29.49, 20.03, 19.87 ppm; $C_{15}H_{20}BrN_5O$ (MW 365.09), LCMS (EI) m/e 366.1 ($M^+$+H).

Step 3. 1-(4-(4-Amino-5-(4-aminophenyl)pyrrolo[1,2-f][1,2,4]triazin-7-yl)piperidin-1-yl)-2-methylpropan-1-one (Compound 5)

A 5-necked 22-L round bottom flask equipped with a mechanical stirrer, a heating mantle, a thermal couple, a reflux condenser, a nitrogen inlet and a nitrogen outlet was charged with 1-(4-(4-amino-5-bromopyrrolo[1,2-f][1,2,4]triazin-7-yl)piperidin-1-yl)-2-methylpropan-1-one (Compound 3, 700 g, 1.911 mol), 4-(4,4,5,5-tetramethyl-1,3,2-dioxaborolan-2-yl) aniline (Compound 4, 502 g, 2.293 mol), and potassium carbonate (528 g, 3.822 mol) in 1-butanol (7.7 L) and water (1.4 L) at room temperature. To the mixture was added chloro(2-dicyclohexylphosphino-2',4',6'-triisopropyl-1,1'-biphenyl)[2-(2'-amino-1,1'-biphenyl)]palladium(II) (XPhos Pd G2, 90 g, 115 mmol) at room temperature. The reaction mixture was degased and refilled with nitrogen before heating up to 80° C. After two hours at 80° C., n-heptane (8 L) was added to the reaction mixture. The resulting slurry was cooled to room temperature. The solids were collected by filtration, and washed with water (6 L). The cake was dried on the filter under house vacuum for 72 hours to provide 1-(4-(4-amino-5-(4-aminophenyl)pyrrolo[1,2-f][1,2,4]triazin-7-yl)piperidin-1-yl)-2-methylpropan-1-one (Compound 5, 648 g, 90%) as a brown solid. $^1$H NMR (500 MHZ, DMSO-$d_6$) δ 7.85; (s, 1H), 7.09; (d, J=8.4 Hz, 2H), 6.65; (d, J=8.4 Hz, 2H), 6.43; (s, 1H), 5.24; (s, 2H), 4.53; (d, J=12.6 Hz, 1H), 4.04; (d, J=13.1 Hz, 1H), 3.38; (ddd, J=11.8, 8.2, 3.8 Hz, 1H), 3.16; (t, J=12.7 Hz, 1H), 2.87; (p, J=6.7 Hz, 1H), 2.71-2.66; (m, 1H), 2.08-2.00; (m, 2H), 1.61-1.58; (m, 2H), 1.02; (d, J=6.5 Hz, 3H), 1.00; (d, J=6.5 Hz, 3H) ppm; $^{13}$C NMR (126 MHz, DMSO-$d_6$) δ 174.51, 156.31, 148.51, 147.65, 133.98, 130.35, 122.57, 119.37, 114.57, 109.67, 108.85, 45.48, 41.81, 32.97, 31.50, 30.56, 29.50, 20.06, 19.89 ppm; $C_{21}H_{26}N_6O$ (MW 378.48), LCMS (EI) m/e 379.2 ($M^+$+H).

Step 4. N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide (Compound I)

In a 5-necked 22-L round bottom flask equipped with a mechanical stirrer, a thermal couple, a nitrogen inlet and a nitrogen outlet were placed 1-(4-(4-amino-5-(4-aminophenyl)pyrrolo[1,2-f][1,2,4]triazin-7-yl)piperidin-1-yl)-2-methylpropan-1-one (Compound 5, 944 g, 2.494 mol), and 1-isopropyl-2,4-dioxo-3-(pyridin-2-yl)-1,2,3,4-tetrahydropyrimidine-5-carboxylic acid hydrochloride (Compound 6, 801 g, 2.569 mol) in tetrahydrofuran (THF, 10 L) at room temperature. The reaction mixture was added triethylamine ($NEt_3$, 0.695 L, 4.988 mol). Upon the completion of the reaction, the reaction mixture was divided evenly into two 22-L round bottom flasks. To each flask was charged water (8 L) at room temperature. The solids were collected by filtration. The resulting wet cake was put back into a 22-L round bottom flask. To the flask was charged THF (3.2 L) and water (10.5 L). The slurry was heated to 55° C., and agitated at 55° C. for two hours. The solids were collected by filtration at 30° C., and washed with water (8 L). The cake was dried on the filter under house vacuum for 72 hours to provide N-(4-(4-amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide (1425 g, 90%) as light brown solid. $^1$H NMR (500 MHZ, DMSO-$d_6$) δ 10.82; (s, 1H), 8.71; (s, 1H), 8.64; (ddd, J=4.8, 1.8, 0.8 Hz, 1H), 8.06; (td, J=7.7, 1.9 Hz, 1H), 7.91; (s, 1H), 7.77; (d, J=8.6 Hz, 2H), 7.60-7.53; (m, 2H), 7.43; (d, J=8.6 Hz, 2H), 6.58; (s, 1H), 4.78; (hept, J=6.8 Hz, 1H), 4.54; (d, J=12.3 Hz, 1H), 4.06; (d, J=12.5 Hz, 1H), 3.40; (tt, J=11.7, 3.5 Hz, 1H), 3.20; (t, J=12.3 Hz, 1H), 2.91; (hept, J=6.7 Hz, 1H), 2.69; (t, J=12.3 Hz, 1H), 2.06; (dd, J=27.7, 12.3 Hz, 2H), 1.61; (q, J=11.8 Hz, 1H), 1.55-1.47; (m, 1H), 1.44; (d, J=6.8 Hz, 6H), 1.02; (d, J=6.8 Hz, 3H), 1.00; (d, J=6.8 Hz, 3H) ppm; $^{13}$C NMR (126 MHz, DMSO-$d_6$) δ 174.51, 163.02, 160.31, 156.20, 150.18, 149.98, 149.18, 148.08, 147.79, 139.55, 137.51, 134.45, 131.24, 130.23, 125.09, 124.57, 120.46, 117.98, 109.90, 109.35, 105.27, 51.17, 45.46, 41.79, 32.97, 31.48, 30.54, 29.49, 21.09 (2-$CH_3$), 20.07, 19.89 ppm; $C_{34}H_{37}N_9O_4$ (MW 635.73), LCMS (EI) m/e 636.3 ($M^+$+H).

Step 5. N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide Maleate (Compound I Maleate)

In a 50-L reactor equipped with a mechanical stirrer, a heating jacket, a thermal couple, a reflux condenser, a nitrogen inlet and a nitrogen outlet was placed N-(4-(4-amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide (Compound I, 1401 g, 2.204 mol) in methanol (MeOH, 10 L) and dichloromethane (DCM, 20 L) at room temperature. The slurry was heated to 50° C. to provide a solution. To the solution was added activated carbon (70 g) and silica gel (70 g). After stirring for 2 hours at 50° C., the mixture was filtered through a Celite pad. To the filtrate was added maleic acid (269 g, 2.314 mol). Most of the DCM was distilled out under atmospheric pressure. Solids gradually precipitated out. The solids were collected by filtration at 18° C., and washed with MeOH (3 L). The cake was dried on the filter under house vacuum for 72 hours to provide N-(4-(4-amino-7-(1-isobutyrylpiperidin-4-yl) pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleate (Compound I maleate, 1425 g, 86%) as an off-white solid. $^1$H NMR (400 MHz, DMSO-$d_6$) δ 10.83; (s, 1H), 8.71; (s, 1H), 8.65-8.63; (m, 1H), 8.06; (td, J=7.8, 1.9 Hz, 1H), 7.95; (s, 1H), 7.77; (d, J=8.6 Hz, 2H), 7.58-7.55; (m, 2H), 7.44; (d, J=8.5 Hz, 2H), 6.62; (s, 1H), 6.25 (s, 2H), 4.78; (hept, J=6.7 Hz, 1H), 4.54; (d, J=12.3 Hz, 1H), 4.06; (d, J=12.5 Hz, 1H), 3.40; (tt, J=11.6, 3.2 Hz, 1H), 3.20; (t, J=12.3 Hz, 1H), 2.90; (hept, J=6.6 Hz, 1H), 2.69; (t, J=12.1 Hz, 1H), 2.09-2.01; (m, 2H), 1.65-1.57; (m, 1H), 1.56-1.49; (m, 1H), 1.44; (d, J=6.8 Hz, 6H), 1.02; (d, J=5.5 Hz, 3H), 1.00; (d, J=5.5 Hz, 3H) ppm; $^{13}$C NMR (101 MHZ, DMSO) δ 174.52, 167.21, 163.03, 160.33, 155.20, 150.18, 149.99, 149.18, 148.07, 146.26, 139.55, 137.67, 135.32, 131.34, 130.87, 130.22, 125.09, 124.57, 120.49, 119.30, 109.80, 109.47, 105.26, 51.17, 45.43, 41.76, 32.97, 31.45, 30.53, 29.50, 21.09 (2-CH$_3$), 20.06, 19.89 ppm; $C_{34}H_{37}N_9O_4$ (free base, MW 635.73), LCMS (EI) m/e 636.3 (M$^+$+H).

Example 5. Synthesis of tert-Butyl 4-(4-amino-5-bromopyrrolo[1,2-f][1,2,4]triazin-7-yl)piperidine-1-carboxylate (Compound 1 of Scheme 1)

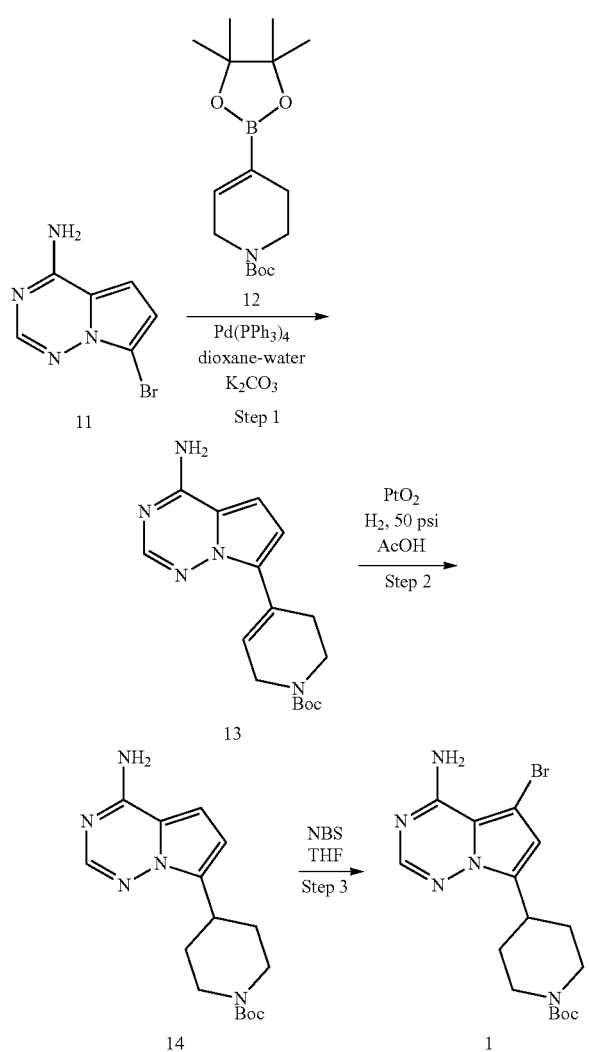

Step 1. tert-Butyl 4-(4-aminopyrrolo[1,2-f][1,2,4]triazin-7-yl)-5,6-dihydropyridine-1 (2H)-carboxylate (Compound 13)

A 3-L round bottom flask equipped with a mechanical stirrer, a heating mantle, a thermal couple, a reflux condenser, a nitrogen inlet and a nitrogen outlet was charged with 7-bromopyrrolo[1,2-f][1,2,4]triazin-4-amine (Compound 11, 100 g, 469 mmol) and tert-butyl 4-(4,4,5,5-tetramethyl-1,3,2-dioxaborolan-2-yl)-5,6-dihydropyridine-1 (2H)-carboxylate (Compound 12, 174 g, 563 mmol) in 1,4-dioxane (876 mL) at room temperature. To the reaction flask was added potassium carbonate (130 g, 939 mmol) and water (218 g) in sequence. The mixture was degassed by exposure to vacuum and refilled with nitrogen atmosphere for three times. After the addition of tetrakis(triphenylphosphine)palladium (0) (Pd(PPh$_3$)$_4$, 13.56 g, 11.7 mmol), the reaction mixture was degassed and refilled with nitrogen for three times at room temperature. Then the reaction mixture was heated to 85-90° C., and agitated at that temperature for 16 hours. Upon the completion of the reaction, water (900 mL) was added in 30 minutes while the internal temperature was above 50° C. The mixture was cooled to room temperature. Solids gradually precipitated out. The solids were collected by filtration at 18° C., and washed with water (2×250 mL) and methyl tert-butyl ether (MTBE, 3×200 mL). The wet cake was put back into the reaction flask, and agitated in MTBE (750 mL) at 50° C. for 1 hour. The solids were collected at room temperature by filtration. The cake was dried in a vacuum oven at 50° C. under vacuum with nitrogen sweeping for 72 hours to provide tert-butyl 4-(4-aminopyrrolo[1,2-f][1,2,4]triazin-7-yl)-5,6-dihydropyridine-1(2H)-carboxylate (Compound 13, 123.7 g, 84%) as a brown solid. $^1$H NMR (500 MHz, DMSO-d$_6$) δ 7.89; (s, 1H), 7.69; (s, 2H), 7.00; (s, 1H), 6.91; (d, J=4.6 Hz, 1H), 6.69; (d, J=4.5 Hz, 1H), 4.06; (s, 2H), 3.55; (t, J=5.5 Hz, 2H), 2.59-2.52; (m, 2H), 1.43; (s, 9H) ppm; $C_{16}H_{21}N_5O_2$ (MW 315.37), LCMS (EI) m/e 316.1 (M$^+$+H).

Step 2. tert-Butyl 4-(4-aminopyrrolo[1,2-f][1,2,4]triazin-7-yl)piperidine-1-carboxylate (Compound 14)

A 2-L flask was charged with tert-butyl 4-(4-aminopyrrolo[1,2-f][1,2,4]triazin-7-yl)-5,6-dihydropyridine-1(2H)-carboxylate (Compound 13, 50.0 g, 159 mmol) and platinum (IV) oxide (10.0 g, 44 mmol) in acetic acid (1000 mL) at room temperature. The flask was put on a Parr Shaker with hydrogen gas at 50 psi. After 16 hours, the reaction mixture was filtered through a Celite pad (50 g), and washed with methanol (500 mL). The filtrate was concentrated under reduced pressure. To the residue was added methyl tert-butyl ether (MTBE, 600 mL) at room temperature. A solution of potassium carbonate (about 50 g) in water (1200 mL) was added to the MTBE solution to adjust the pH value to 6-7. The solids were collected by filtration, and washed with water (2×300 mL) and n-heptane (2×300 mL). The cake was dried in a vacuum oven at 50° C. under vacuum with nitrogen sweeping for 16 hours to provide tert-butyl 4-(4-aminopyrrolo[1,2-f][1,2,4]triazin-7-yl)piperidine-1-carboxylate (Compound 14, 49.3 g, 98%) as a light brown solid. $^1$H NMR (500 MHZ, DMSO-d$_6$) δ 7.82; (s, 1H), 7.59; (s, 2H), 6.81; (d, J=4.4 Hz, 1H), 6.44; (d, J=4.3 Hz, 1H), 4.05; (d, J=11.3 Hz, 2H), 3.25; (tt, J=11.8, 3.3 Hz, 1H), 2.88; (s, 2H), 1.95; (d, J=11.9 Hz, 2H), 1.51; (qd, J=12.6, 4.0 Hz, 2H), 1.42; (s, 9H) ppm; $C_{16}H_{23}N_5O_2$ (MW 317.39), LCMS (EI) m/e 318.1 (M$^+$+H).

Step 3. tert-Butyl 4-(4-amino-5-bromopyrrolo[1,2-f][1,2,4]triazin-7-yl)piperidine-1-carboxylate (Compound 1)

A 5-necked 22-L round bottom flask equipped with a mechanical stirrer, a thermal couple, a reflux condenser, a nitrogen inlet and a nitrogen outlet was charged with tert-butyl 4-(4-aminopyrrolo[1,2-f][1,2,4]triazin-7-yl)piperidine-1-carboxylate (Compound 14, 730 g, 2.30 mol) in tetrahydrofuran (THF, 14.0 L) at room temperature. The mixture was cooled to 0-5° C. To the reaction mixture was added N-bromosuccinimide (NBS, 409 g, 2.30 mol) in 5 minutes while the internal temperature was maintained below 15° C. After 1 hour of agitation at below 10° C., some solvents (9.0 L) were removed under reduced pressure. To the residual solution was addeded a solution of sodium bicarbonate (140 g, 1.67 mol) in water (14.0 L) over 5 minutes. Solids precipitated out. The solids were collected by filtration, and washed with water (7.0 L) and n-heptane (4 L). The wet cake was dried on the filter under house vacuum for 48 hours to provide tert-butyl 4-(4-amino-5-bromopyrrolo[1,2-f][1,2,4]triazin-7-yl)piperidine-1-carboxylate (Compound 1, 886 g, 97%) as a brown solid. $^1$H NMR (400 MHZ, DMSO-d$_6$) δ 7.86; (s, 1H), 6.66; (s, 1H), 4.04; (d, J=11.0 Hz, 2H), 3.30-3.23; (m, 1H), 2.86; (br.s, 2H), 1.92; (d, J=12.4 Hz, 2H), 1.50; (qd, J=12.8, 4.1 Hz, 2H), 1.41; (s, 9H) ppm; $^{13}$C NMR (101 MHZ, DMSO-d$_6$) δ 155.68, 154.29, 148.35, 135.37, 111.31, 110.68, 87.29, 79.10, 43.97, 32.63, 30.37, 28.58 ppm; $C_{16}H_{22}BrN_5O_2$ (MW 395.10), LCMS (EI) m/e 396.1 (M$^+$+H).

Example 6. Synthesis of 1-Isopropyl-2,4-dioxo-3-(pyridin-2-yl)-1,2,3,4-tetrahydropyrimidine-5-carboxylic acid (Compound 6 of Scheme 1)

Step 3: Diethyl 2-((3-pyridin-2-ylureido)methylene)malonate

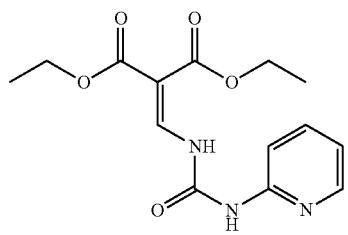 [SMILES: CCOC(=O)C(=CNC(=O)Nc1ccccn1)C(=O)OCC]

To a mixture of diethyl 2-(aminomethylene) malonate (3.0 g, 16.0 mmol) and 2-isocyanatopyridine (2.02 g, 16.8 mmol) in 1,2-dichloroethane (9.0 mL) at rt was added N,N-diisopropylethylamine (3.6 mL, 20.8 mmol). The reaction mixture was then stirred at 70° C. overnight, cooled to rt, and directly purified via column chromatography (0% to 15% MeOH in CH$_2$Cl$_2$) to give the product (3.18 g, 65%). LCMS calcd for $C_{14}H_{18}N_3O_5$ (M+H)$^+$: m/z=308.1. Found: 308.1.

Step 4: 1-Isopropyl-2,4-dioxo-3-(pyridin-2-yl)-1,2,3,4-tetrahydropyrimidine-5-carboxylic Acid

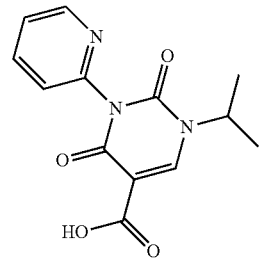 [SMILES: CC(C)n1cc(C(=O)O)c(=O)n(-c2ccccn2)c1=O]

A mixture of diethyl 2-((3-(pyridin-2-yl)ureido)methylene)malonate (3.18 g, 10.4 mmol) and 2.5 M NaOEt in EtOH (6.2 mL, 15.5 mmol) in EtOH (25 mL) was stired at rt for 3 h. The resulting mixture was diluted with EtOAc, and washed/acidified with 1 N citric acid solution (30 mL). The organic layer was separated, and the aqueous layer was further extracted with 3:1 CHCl$_3$/isopropyl alcohol (30 mL×3). The combined organic layers were dried over Na$_2$SO$_4$, and concentrated to provide the crude product, ethyl 2,4-dioxo-3-(pyridin-2-yl)-1,2,3,4-tetrahydropyrimidine-5-carboxylate, which was used directly in the next step. LCMS calcd for $C_{12}H_{12}N_3O_4$ (M+H)$^+$: m/z=262.1. Found: 262.2.

A mixture of crude ethyl 2,4-dioxo-3-(pyridin-2-yl)-1,2,3,4-tetrahydropyrimidine-5-carboxylate from previous step, 2-iodopropane (2.06 mL, 20.7 mmol), and Cs$_2$CO$_3$ (10.1 g, 31.0 mmol) in DMF (35 mL) was stirred at 70° C. for 3 h. The reaction mixture was then cooled to rt, diluted with 3:1 CHCl$_3$/isopropyl alcohol (75 mL), washed with water, brine, dried over Na$_2$SO$_4$, and concentrated to afford the crude product, ethyl 1-isopropyl-2,4-dioxo-3-(pyridin-2-yl)-1,2,3,4-tetrahydropyrimidine-5-carboxylate, which was used directly in the next step. LCMS calcd for $C_{15}H_{18}N_3O_4$ (M+H)$^+$: m/z=304.1. Found: 304.1.

A mixture of crude ethyl 1-isopropyl-2,4-dioxo-3-(pyridin-2-yl)-1,2,3,4-tetrahydropyrimidine-5-carboxylate from previous step in 4 M HCl in 1,4-dioxane (20 mL, 82 mmol) and water (5.0 mL) was stirred at 80° C. for 5 h, cooled to rt, and concentrated. The resulting material was then purified via column chromatography (0% to 15% MeOH in CH$_2$Cl$_2$) to give the product as a slightly yellow solid (1.50 g, 47% three steps). LCMS calcd for $C_{13}H_{14}N_3O_4$ (M+H)$^+$: m/z=276.1. Found: 276.1.

Example 7. Solid State Characterization of N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide Maleate (Compound I Maleate)

X-Ray Powder Diffraction (XRPD) of Compound I Maleate

The X-Ray Powder Diffraction (XRPD) was obtained from Rigaku MiniFlex X-ray Powder Diffractometer (XRPD). The general experimental procedures for XRPD were: (1) X-ray radiation from copper at 1.054056 Å with K$_β$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min. The XRPD pattern is shown in FIG. 1 and the XRPD data are provided in Table 6A.

TABLE 6A

XRPD Data: Maleate of the Compound I

| 2-Theta (°) | Height | H % |
|---|---|---|
| 4.3 | 5452 | 89.8 |
| 5.8 | 63 | 1.0 |
| 8.4 | 6068 | 100 |
| 12.6 | 177 | 2.9 |
| 13.2 | 331 | 5.5 |
| 15.8 | 120 | 2.0 |
| 17.1 | 132 | 2.2 |
| 18.5 | 230 | 3.8 |
| 20.3 | 136 | 2.2 |
| 20.9 | 89 | 1.5 |
| 23.1 | 114 | 1.9 |
| 24.0 | 118 | 1.9 |
| 25.2 | 137 | 2.3 |
| 28.4 | 45 | 0.7 |
| 29.7 | 44 | 0.7 |
| 31.5 | 59 | 1.0 |
| 35.7 | 102 | 1.7 |
| 42.6 | 40 | 0.7 |

Differential Scanning Calorimetry (DSC) of Compound I Maleate

The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min. The DSC thermogram is shown in FIG. 2. The DSC thermogram revealed a major endothermal event at an onset temperature of 202.9° C. with a peak temperature of 211.0° C. which is believed to be the melting and decomposition temperature of the compound.

Thermogravimetric Analysis (TGA) of Compound I Maleate

The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan. The TGA thermogram is shown in FIG. 3. A weight loss of about 0.7% up to 150° C. was observed and believed to be associated with the loss of moisture and residual solvents. The compound starts to decompose significantly at above 200° C.

Other Crystalline Salts

Other crystalline salts of the Compound I such as HCl salt, mono-sulfate salt, hemi-sulfate salt, mesylate salt, and besylate salt have been discovered and prepared.

Example A

Axl Autophosphorylation Assay

Autophosphorylation of Axl was carried out by incubating the recombinant Axl protein (Life Technologies, PV4275) in buffer containing 50 mM Tris, pH7.5, 0.2 mg/ml Axl, 5 mM ATP, 20 mM $MgCl_2$ and 2 mM DTT at room temperature for 1 hour.

TAM Enzymatic Assay

The kinase assay buffer contained 50 mM HEPES, pH7.5, 10 mM MgCl2, 1 mM EGTA, 0.01% NP-40 and 2 mM DTT. 0.1 ul test compounds dissolved in DMSO were transferred from compound plates to white 384-well assay plates (Greiner LUMITRAC plates). The final concentration of DMSO was 1.25%. Enzyme solutions of 5.1 nM phosphor-Axl, or 0.0625 nM c-Mer (Carna Biosciences, 08-108), or 0.366 nM Tyro3 (Life Technologies, PR7480A) were prepared in assay buffer. A 1 mM stock solution of peptide substrate Biotin-EQEDEPEGDYFEWLE-amide SEQ ID NO: 1 (Quality Controlled Biochemicals, MA) dissolved in DMSO was diluted to 1 uM in assay buffer containing 2000 uM ATP. 4 ul enzyme solution (or assay buffer for the enzyme blank) was added to the appropriate wells in each plate, and then 4 ul/well substrate solution was added to initiate the reaction. The plate was protected from light and incubated at room temperature for 60 min. The reaction was stopped by adding 4 ul detection solution containing 50 mM Tris-HCl, pH7.8, 150 mM NaCl, 0.05% BSA, 45 mM EDTA, 180 nM SA-APC (Perkin Elmer, CR130-100) and 3 nM Eu-W1024 anti-phosphotyrosine PY20 (Perkin Elmer, AD0067). The plate was incubated for 1 h at room temperature, and HTRF (homogenous time resolved fluorescence) signal was measured on a PHERAstar FS plate reader (BMG labtech). Percentage of inhibition was calculated for each concentration and IC50 value was generated from curve fitting with GraphPad Prism software.

The Compound I was found to be an inhibitor of one or more of AXL, MER, and TYRO3. $IC_{50}$ data for the trifluoroacetic acid salt of Compound I are disclosed in U.S. Pat. No. 9,981,975 and are provided below in Table 7A. The symbol "†" indicates an $IC_{50}$ of ≤5 nM, "††" indicates an $IC_{50}$ of >5 nM but ≤10 nM. and "†††" indicates an $IC_{50}$ of >10 nM but ≤100 nM.

TABLE 7A

| Compound | Axl $IC_{50}$ (nM) | Mer $IC_{50}$ (nM) | Tyro3 $IC_{50}$ (nM) |
|---|---|---|---|
| Compound I trifluoroacetic acid salt | † | † | ††† |
| Compound I maleic acid salt | † | † | ††† |

Example B. Generation of BAF3-AXL, BAF3-MER and BAF3-TYRO3 Cells and Cell Proliferation Assay The cytoplasmic domain of AXL, MER, or TYRO3 fused with dimerization sequence and HA tag is cloned into pMSCV vector with puromycin-resistance marker to generate three constructs (pMSCV-AXL, pMSCV-MER and pMSCV-TYRO3). BAF3 cells are transfected with the three constructs individually by electroporation. Single clones that are IL3 independent and puromycin-resistant are selected and characterized. Cells with stable expression of AXL, MER, or TYRO3 are selected and designated BAF3-AXL, BAF3-MER and BAF3-TYRO3 cells.

BAF3, BAF3-AXL, BAF3-MER or BAF3-TYRO3 cells lines are maintained in RPMI1640 with 10% FBS (Gibco/Life Technologies, Carlsbad, CA). To measure the effect of test compounds on cell viability, 1000 cells/well are plated into 384 well tissue culture plates in growth medium with a serial dilution of compound or DMSO alone for 48 hours at 37° C. with 5% $CO_2$, cell viability is measured by ATP assay (CellTiter-Glo Assay, Promega) according to the manufacturer's procedure. The data are converted to percent inhibition relative to DMSO control and $IC_{50}$ curves are fitted using GraphPad Prism software.

Example C. BaF3-AXL ELISA and BaF3-MER ELISA

BaF3-AXL or BaF3-MER cells are maintained in culture medium RPMI with 10% FBS and puromycin (1 µg/ml, Gibco/Life Technologies, Carlsbad, CA). To measure the effect of test compounds on phosphor-AXL or phosphor-MER, the cells are plated ($5\times10^4$ cells/well) in a V-bottom polypropylene plate (Greiner bio-one) in the presence or absence of test compounds diluted in culture medium, and incubated for 1 hour at 37° C. with 5% $CO_2$. The cells are harvested by centrifugation, and lysed in 110 µl of ice cold lysis buffer (Cell Signaling) with protease and phosphatase inhibitors (Halts PI, Thermo Fisher) for 30 min on ice. The cell lysate is stored at −80° C. for ELISA. ELISA plates are prepared by incubating Costar plate with anti-HA antibody (1 µg/ml) for 1 hour at room temperature. The plates are washed and blocked with PBS with 3% BSA. Cell lysate are loaded onto ELISA plate and incubated at 4° C. overnight. The plates are washed and incubated with LANCE Eu-W1024 anti-phospho-tyrosine antibody (PY-20) (Perkin Elmer) in DELFIA assay buffer (Perkin Elmer) for 1 hour, and read on the Pherastar (BMG Labtech). The data is converted to percent inhibition relative to DMSO control and $IC_{50}$ determination is performed by fitting the curve of percent inhibition versus the log of the inhibitor concentration using GraphPad Prism.

Example D. H1299 Phospho-AXL ELISA

H1299 cells (ATCC), human non-small cell lung carcinoma cell line with Axl expression, are maintained in culture medium RPMI with 10% FBS (Gibco/Life Technologies, Carlsbad, CA). To measure the effect of test compounds on phosphor-AXL, the cells are plated (30000 cells/well) in 96 well tissue culture plates (Costar) and incubated overnight at 37° C. with 5% $CO_2$. Compounds at an appropriate concentration are added and incubated for 1 hour at 37° C. with 5% $CO_2$. rhGas6 (R&D Systems, 6 µg/ml) are added to each well. Plates are incubated at 37° C. with 5% $CO_2$ for 15 min. Cells are harvested and lysed in 110 µL of ice cold lysis buffer (Cell Signaling) with protease and phosphatase inhibitors (Halts PI, Thermo Fisher). The lysate is incubated for 1 hour on ice and stored at −80° C. for ELISA. ELISA plates are prepared by incubating Costar plate with anti-HA antibody (1 µg/ml) for 1 hour at room temperature. The plates are washed and blocked with PBS with 3% BSA. Cell lysate is loaded onto ELISA plates and incubated at 4° C. overnight. The plates are washed and incubated with LANCE Eu-W1024 anti-phospho-tyrosine antibody (PY-20) (Perkin Elmer) in DELFIA assay buffer (Perkin Elmer) for 1 hour, and read on the Pherastar (BMG Labtech). The data is converted to percent inhibition relative to DMSO control and $IC_{50}$ determination is performed by fitting the curve of percent inhibition versus the log of the inhibitor concentration using GraphPad Prism.

Example E. Whole Blood H1299 Phospho-AXL ELISA

H1299 Cells (ATCC) are maintained in culture medium RPMI with 10% FBS (Gibco/Life Technologies, Carlsbad, CA). To measure the effect of test compounds on phospho-AXL in whole blood, the cells are plated (30000 cells/well) in 96 well tissue culture plates (Costar) and incubated overnight at 37° C. with 5% $CO_2$. Blood obtained from normal donors is mixed with test compounds for 1 hour. Culture medium is removed from H1299 cells, and blood with compound is added to each well. After 1 hour incubation at 37° C. with 5% $CO_2$, rh-Gas6 (4 µg/ml, R&D Systems) is added to each well. The plate is incubated at 37° C. with 5% $CO_2$ for 15 min. The cells are washed with PBS, and lysed in 110 uL of ice cold lysis buffer (Cell Signaling) with protease and phosphatase inhibitors (Halts PI, Thermo Fisher) for 1 hour on ice. The plate is stored at −80° C. for ELISA. ELISA plates are prepared by incubating Costar plate with anti-HA antibody (1 ug/ml) for 1 hour at room temperature. The plates are washed and blocked with PBS with 3% BSA. Cell lysate are loaded onto ELISA plate and incubated at 4° C. overnight. The plates are washed and incubated with LANCE Eu-W1024 anti-phospho-tyrosine antibody (PY-20) (Perkin Elmer) in DELFIA assay buffer (Perkin Elmer) for 1 hour, and read on the Pherastar (BMG Labtech). The data is converted to percent inhibition relative to DMSO control and $IC_{50}$ determination is performed by fitting the curve of percent inhibition versus the log of the inhibitor concentration using GraphPad Prism.

Example F. G361 Phospho-Akt Cell Insight ELISA

G361 cells (ATCC), human malignant melanoma cell line expressing Mer, are maintained in culture medium RPMI with 10% FBS (Gibco/Life Technologies, Carlsbad, CA). To measure the effect of test compounds on MER signaling pathway, the cells are plated at $2\times10^4$ cells/well in 100 µL volume in 96 well CellBind surface plates (Corning), and incubated overnight at 37° C. with 5% $CO_2$. 20 µL of test compounds at appropriate concentrations are added to the cells and incubated for 1 hour. rhGas6 (4 µg/ml, R&D Systems) is added to each well, and incubated for 20 min. The cells are fixed by adding 50 uL 4% paraformaldehyde (Electron Microscopy Sciences) in PBS (Corning) for 30 min at room temperature. Plates are washed and incubated with 50 uL 0.2% triton X-100 (Sigma) in PBS for 10 minutes at room temperature. Plates are washed and incubated with 100 uL blocking buffer (0.1% BSA in PBS) for 30 min. Plates are washed and incubated with Phospho-AKT (Ser473) (D9E) rabbit mAb (Cell Signaling) diluted in 0.1% BSA (1:300 dilution) at 4° C. overnight. Plates are washed and incubated with 50 uL Alexaflour 488 F(ab')$^2$ fragment of goat anti-rabbit IgG (H+L) (Molecular Probes, 1:1000 dilution) and Hoechst 33342 (Thermo Fisher, 1:2000 dilution) in PBS at room temperature for 2 hours. Plates are washed with PBS, and read on Cell Insight CX5 (Thermo Fisher).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A pharmaceutical formulation in solid oral dosage form comprising:
   (a) N-(4-(4-amino-7-(1-isobutyrylpiperidin-4-yl) pyrrolo [2,1-f][1,2,4]triazin-5-yl)phenyl)-1-isopropyl-2,4-dioxo-3-(pyridin-2-yl)-1,2,3,4-tetrahydropyrimidine-5-carboxamide maleate (Compound I maleate);
   (b) an organic acid; and
   (c) a surfactant;
   wherein the Compound I maleate is in crystalline form.

2. The pharmaceutical formulation of claim 1, wherein the organic acid is citric acid, ascorbic acid, fumaric acid, malic acid, sorbic acid, or tartaric acid.

3. The pharmaceutical formulation of claim 1, wherein the organic acid is citric acid.

4. The pharmaceutical formulation of claim 1, comprising about 1 wt % to about 50 wt % of organic acid.

5. The pharmaceutical formulation of claim 1, comprising about 5 wt % to about 40 wt % of organic acid.

6. The pharmaceutical formulation of claim 1, comprising about 5 wt % to about 30 wt % of organic acid.

7. The pharmaceutical formulation of claim 1, comprising about 10 wt % to about 20 wt % of organic acid.

8. The pharmaceutical formulation of claim 1, comprising about 10 wt % or about 20 wt % of organic acid.

9. The pharmaceutical formulation of claim 1, wherein the surfactant is a poloxamer.

10. The pharmaceutical formulation of claim 1, wherein the surfactant is poloxamer 407 or poloxamer 188.

11. The pharmaceutical formulation of claim 1, wherein the surfactant is poloxamer 407.

12. The pharmaceutical formulation of claim 1, comprising about 1 wt % to about 20 wt % of surfactant.

13. The pharmaceutical formulation of claim 1, comprising about 5 wt % to about 15 wt % of surfactant.

14. The pharmaceutical formulation of claim 1, comprising about 5 wt % to about 10 wt % of surfactant.

15. The pharmaceutical formulation of claim 1, comprising about 1 wt % to about 10 wt % of surfactant.

16. The pharmaceutical formulation of claim 1, further comprising a diluent.

17. The pharmaceutical formulation of claim 16, wherein the diluent is mannitol.

18. The pharmaceutical formulation of claim 16, comprising about 40 wt % to about 90 wt % of diluent.

19. The pharmaceutical formulation of claim 16, comprising about 50 wt % to about 80 wt % of diluent.

20. The pharmaceutical formulation of claim 16, comprising about 50 wt % to about 75 wt % of diluent.

21. The pharmaceutical formulation of claim 1, further comprising a disintegrant.

22. The pharmaceutical formulation of claim 21, wherein the disintegrant is crospovidone.

23. The pharmaceutical formulation of claim 21, comprising about 1 wt % to about 10 wt % of disintegrant.

24. The pharmaceutical formulation of claim 21, comprising about 2 wt % to about 5 wt % of disintegrant.

25. The pharmaceutical formulation of claim 1, further comprising a lubricant, glidant, or both.

26. The pharmaceutical formulation of claim 25, wherein the lubricant is stearic acid.

27. The pharmaceutical formulation of claim 25, comprising about 1 wt % to about 5 wt % of lubricant.

28. The pharmaceutical formulation of claim 25, comprising about 2 wt % of lubricant.

29. The pharmaceutical formulation of claim 25, wherein the glidant is colloidal silica.

30. The pharmaceutical formulation of claim 25, comprising about 0.1 wt % to about 5 wt % of glidant.

31. The pharmaceutical formulation of claim 25, comprising about 0.5 wt % or about 1 wt % of glidant.

32. The pharmaceutical formulation of claim 1, comprising about 1 wt % to about 20 wt % of Compound I maleate.

33. The pharmaceutical formulation of claim 1, comprising about 2 wt % to about 15 wt % of Compound I maleate.

34. The pharmaceutical formulation of claim 1, comprising about 3 wt % or about 12 wt % of Compound I maleate.

35. A pharmaceutical formulation comprising:
   (a) about 2 wt % to about 15 wt % of N-(4-(4-amino-7-(1-isobutyrylpiperidin-4-yl) pyrrolo[2,1-f][1,2,4]triazin-5-yl)phenyl)-1-isopropyl-2,4-dioxo-3-(pyridin-2-yl)-1,2,3,4-tetrahydropyrimidine-5-carboxamide maleate (Compound I maleate);
   (b) about 5 wt % to about 30 wt % of citric acid; and
   (c) about 5 wt % to about 15 wt % a poloxamer;
   wherein the Compound I maleate is in crystalline form.

36. The pharmaceutical formulation of claim 1, wherein the dosage form is a tablet or capsule.

37. The pharmaceutical formulation of claim 1, wherein the dosage form is a capsule.

38. The pharmaceutical formulation of claim 1, wherein Compound I maleate has at least one X-ray powder diffraction ("XRPD") peak, in terms of 2-theta, selected from about 4.3°, about 8.4°, about 12.6°, about 13.2°, and about 18.5°.

39. The pharmaceutical formulation of claim 1, wherein Compound I maleate has at least two XRPD peaks, in terms of 2-theta, selected from about 4.3°, about 8.4°, about 12.6°, about 13.2°, and about 18.5°.

40. The pharmaceutical formulation of claim 1, wherein Compound I maleate has at least three XRPD peaks, in terms of 2-theta, selected from about 4.3°, about 8.4°, about 12.6°, about 13.2°, and about 18.5°.

41. The pharmaceutical formulation of claim 1, wherein Compound I maleate has XRPD peaks, in terms of 2-theta, selected from about 4.3°, about 8.4°, about 12.6°, about 13.2°, and about 18.5°.

42. The pharmaceutical formulation of claim 1, wherein Compound I maleate has an XRPD profile substantially as shown in FIG. 1.

43. The pharmaceutical formulation of claim 1, wherein Compound I maleate has a differential scanning calorimetry ("DSC") thermogram having an endothermic peak at about 211° C.

44. The pharmaceutical formulation of claim 1, wherein Compound I maleate has a DSC thermogram substantially as shown in FIG. 2.

* * * * *

SEQUENCE LISTING

```
Sequence total quantity: 1
SEQ ID NO: 1           moltype = AA  length = 15
FEATURE                Location/Qualifiers
source                 1..15
```

```
                    mol_type = protein
                    organism = synthetic construct
SEQUENCE: 1
EQEDEPEGDY FEWLE                                                                    15
```